United States Patent
Willenberg et al.

(10) Patent No.: US 10,948,491 B2
(45) Date of Patent: Mar. 16, 2021

(54) PASSIVE INSECT SURVEILLANCE SENSOR DEVICE

(71) Applicant: UNIVERSITY OF CENTRAL FLORIDA RESEARCH FOUNDATION, INC., Orlando, FL (US)

(72) Inventors: Bradley J. Willenberg, Orlando, FL (US); Sudipta Seal, Oviedo, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 149 days.

(21) Appl. No.: 15/751,638

(22) PCT Filed: Aug. 11, 2016

(86) PCT No.: PCT/US2016/046496
§ 371 (c)(1),
(2) Date: Feb. 9, 2018

(87) PCT Pub. No.: WO2017/027677
PCT Pub. Date: Feb. 16, 2017

(65) Prior Publication Data
US 2018/0231550 A1 Aug. 16, 2018

Related U.S. Application Data

(60) Provisional application No. 62/203,626, filed on Aug. 11, 2015.

(51) Int. Cl.
*A01M 1/02* (2006.01)
*G01N 33/569* (2006.01)
(Continued)

(52) U.S. Cl.
CPC ......... *G01N 33/56983* (2013.01); *A01M 1/02* (2013.01); *A01M 1/023* (2013.01);
(Continued)

(58) Field of Classification Search
None
See application file for complete search history.

(56) References Cited

U.S. PATENT DOCUMENTS

| 4,908,977 A | * | 3/1990 | Foster | A01M 1/02 43/107 |
| 5,501,033 A | | 3/1996 | Wefler et al. | |

(Continued)

FOREIGN PATENT DOCUMENTS

| WO | 9925826 A1 | 5/1999 |
| WO | 2009075404 A1 | 6/2009 |
| WO | 2014035993 A2 | 3/2014 |

OTHER PUBLICATIONS

International Search Report and Written Opinion issued in International Application No. PCT/US2016/046496 dated Oct. 24, 2016.
(Continued)

*Primary Examiner* — Rebecca M Giere
(74) *Attorney, Agent, or Firm* — Meunier Carlin & Curfman LLC

(57) ABSTRACT

Disclosed are real-time insect surveillance sensor devices and methods that use a colorimetric readout for detecting insect disease vectors (such as mosquitoes which can transmit pathogens such as DENV, CHIKV, and ZIKV). The method involves an attractive or feeding solution combined with detector conjugates. The conjugate can specifically detect proteins present in insect saliva and/or proteins specific to mosquito-borne pathogens.

12 Claims, 8 Drawing Sheets

(51) Int. Cl.
  G01N 33/577 (2006.01)
  G01N 33/58 (2006.01)
  A01M 1/10 (2006.01)
(52) U.S. Cl.
  CPC ............ *A01M 1/026* (2013.01); *A01M 1/106* (2013.01); *G01N 33/569* (2013.01); *G01N 33/577* (2013.01); *G01N 33/585* (2013.01); *G01N 2333/185* (2013.01); *G01N 2333/43591* (2013.01); *Y02A 50/30* (2018.01)

(56) References Cited

U.S. PATENT DOCUMENTS

| | | | |
|---|---|---|---|
| 8,026,108 | B1 | 9/2011 | Huo et al. |
| 8,883,094 | B2 | 11/2014 | Huo et al. |
| 9,005,994 | B2 | 4/2015 | Huo |
| 2004/0053222 | A1 | 3/2004 | Storhoff et al. |
| 2014/0200337 | A1 | 7/2014 | Bruno et al. |
| 2015/0020439 | A1 | 1/2015 | Willenberg et al. |

OTHER PUBLICATIONS

CDC. Table 1. Laboratory-confirmed chikungunya virus disease cases reported to ArboNET by state. Feb. 2015.
CDC-U.S. Centers for Disease Control and Prevention. Locally acquired dengue—KeyWest F, 2009-2010. Morb. Mortal. Wkly. Rep. 59:577-581, 2010.
WHO. A global brief on vector-borne diseases. Geneva, Switzerland, 2014.
Agnihotri, et al., Design of Aptamer-Gold Nanoparticles Based Colorimetric Assay for the Early Diagnosis of Breast Tumor, International Journal of Science and Research (IJSR), vol. 3, Issue 11, Nov. 2014, pp. 1703-1707.
Bernier, et al., "Synergistic attraction of *Aedes aegypti* (L.) to binary blends of L-lactic acid and acetone, dichloromethane, or dimethyl disulfide", J. Medical Entomology 40(5):653-656, 2003.
Bhatt, "The global distribution and burden of dengue.", Nature 496(7446):504-507, 2013.
Bhatta, et al., "Cationic surface reconstructions on cerium oxide nanocrystals: An aberration corrected HRTEM study.", ACS NANO, 6(1): 421-430, 2012.
Bullivant, et al., "Materials characterization of feraheme/ferumoxytol and preliminary evaluation of its potential for magnetic fluid hyperthermia", International Journal of Molecular Sciences, 14(9):17501-17510, 2013.
Chen, et al., "Rare earth nanoparticles prevent Retinal degeneration induced by intracellular peroxides.", Nature Nanotechnology, 1(2):142-150, 2006.
Cheung "Development of aptamer-nanoparticle conjugates as a new approach to", University of Hong Kong; 2012.
Ci W. "The role of immunity to mosquito salivary proteins in the pathogenesis of flaviviruses", Colorado State University; 2007.
Das, et al., "The induction of angiogenesis by cerium oxide nanoparticles through the modulation of oxygen in intracellular environments.", Biomaterials 33(31):7746-7755, 2012.
Das, et al., "Therapeutic potential of nanoceria in regenerative medicine", MRS Bulletin, Nov., 39(11): 976-983, 2014.
Deka, et al., "Sensitive Protein Assay with Distinction of Conformations Based on Visible Absorption Changes of Citrate-Stabilized Gold Nanoparticles", J of Physical Chem 113:17, 2009.
Della Rocca, et al., "A degradable, bioactive, gelatinized alginate hydrogel to improve stem cell/growth factor delivery and facilitate healing after myocardial infarction.", Medical Hypotheses, 79(5), 673-7, 2012.

Ellington, et al., "In vitro selection of RNA molecules that bind specific ligands.", Nature 346:818-822, 1990.
Guzman, "Dengue: a continuing global threat.", Nature Reviews Microbiology 2010: S7-S16.
Hall-Mendelin, et al., "Exploiting mosquito sugar feeding to detect mosquito-borne pathogens.", Proc. Natl. Acad. Sci. USA 107(25):11255-11259, 2010.
Jeon, et al., "A colorimetric aptasensor for the diagnosis of malaria based on cationic polymers and gold nanoparticles", Analytical Biochemistry 439(1):11-16, 2013.
Kline, et al., "Efficacy of three attractant blends tested in combination with carbon dioxide against natural populations of mosquitoes and biting flies at the lower Suwannee wildlife refuge.", J. Amer. Mosquito Control Assoc. 28(2):123-127, 2012.
Lee, et al., "Cationic Surfactant-Based Colorimetric Detection of Plasmodium Lactate Dehydrogenase, a Biomarker for Malaria, Using the Specific DNA Aptamer.", Plos One 9(7), 2014.
Luo, et al., "An aptamer-based fluorescence biosensor for multiplex detection using unmodified gold nanoparticles.", Chemical Communications 48(51):6387-6389, 2012.
McCormack, et al., "Inhibition of Nanoceria's Catalytic Activity due to Ce3+ Site Specific Interaction with Phosphate Ions.", J. Phys. Chem. C, 118:18992-19006, 2014.
Okumu, et al., "Development and Field Evaluation of a Synthetic Mosquito Lure That Is More Attractive than Humans.", PLoS ONE 5(1): e8951. doi:10.1371/journal.pone.0008951, Journal of Medical Entomology, 47(2):274-282. 2010, Journal of the American Mosquito Control Association, 28(2):123-127. 2012.
Owhashi, et al., "The role of saliva of Anopheles stephensi in inflammatory response: identification of a high molecular weight neutrophil chemotactic factor.", Parasitology Research 87(5):376-382, 2001.
Schwartz, et al., "Biology and pathogenesis of chikungunya virus.", Nature Reviews Microbiology 8(7):491-500, 2010.
Song, et al., "Aptamers and Their Biological Applications.", Sensors 12(1):612-631, 2012.
Staples, et al., "Chikungunya Fever: An Epidemiological Review of a Re-Emerging Infectious Disease.", Clinical Infectious Diseases 49(6):942-948, 2009.
Storhoff, et al., "One-pot colorimetric differentiation of polynucleotides with single base imperfections using gold nanoparticle probes", J. Am. Chem. Soc. 120(9):1959-1964, 1998.
Tuerk, et al., "Systematic evolution of ligands by exponential enrichment: RNA ligands to bacteriophage T4 DNA polymerase", Science 249:505-510, 1990.
Vazquez, et al., "Polymer-coated cannulas for the reduction of backflow during", J. Materials Science: Materials in Medicine, 23(8):2037-46, 2012.
Willenberg, et al., "Gelatinized copper-capillary alginate gel functions as an injectable tissue scaffolding system for stem cell transplants.", J. Biomaterials Science 22:1621-1637, 2011.
Willenberg, et al., "Self-assembled coppercapillary alginate gel scaffolds with oligochitosan support embryonic stem cell growth", J. Biomedical Materials Research Part A 79A(2): 440-450, 2006.
Willenberg, Bradley J. et al., "Colorimetric Sensor Devices Using Aptamer-Gold Nanoparticle Conjugates for Field Surveillance of Mosquito-Borne Diseases".
Wong, et al., "Defining the Catalytic Activity of Nanoceria in the P23H-1 Rat, a Photoreceptor Degeneration Model.", PLoS ONE 10(3): e0121977, 2015.
Xia, et al., "Colorimetric detection of DNA, small molecules, proteins, and ions using unmodified gold nanoparticles and conjugated polyelectrolytes", PNAS 107:24, 2010, 10837-10841.
Zheng, et al., "Aptamer-based colorimetric biosensing of dopamine using unmodified gold nanoparticles.", Sensors and Actuators B-Chemical 156(1):95-99, 2011.

\* cited by examiner

PASSIVE INSECT SURVEILLANCE SENSOR DEVICE

CROSS REFERENCE TO RELATED APPLICATIONS

This application is a national stage application filed under 35 U.S.C. § 371 of PCT/US2016/046496 filed Aug. 11, 2016, which claims the benefit of U.S. Provisional Patent Application Ser. No. 62/203,626 filed Aug. 11, 2015, each of which are expressly incorporated herein by reference in their entirety.

FIELD

The invention is directed to devices and methods for insect surveillance and pathogen detection.

BACKGROUND OF THE INVENTION

Dengue virus (DENV) is a single-stranded mosquito-borne RNA virus that is a member of the Flaviviridae family, genus *flavivirus*, which has four distinct serotypes known as DENV 1-4. It is responsible for dengue fever, characterized by high fever, debilitating headache, malaise, nausea, vomiting, body aches, swollen glands and rash, all of which are temporary and resolve within a week or two. Though there is no cure for dengue fever, and a vaccine is still in clinical trials, the disease is rarely fatal if well-managed. In a small amount of cases (about 1% annually), the disease takes on a more sinister form as dengue shock syndrome (DSS)/dengue hemorrhagic fever (DHF) and does result in an estimated 22,000 deaths, most of which are children.

The vast majority of the dengue fever cases documented in the continental United States are travel-associated or imported with travelers acquiring the disease while visiting foreign lands where dengue is endemic and then returning/immigrating to the US. However, locally-transmitted DENV has occurred in Texas, Hawaii and Florida. DENV is a global threat with over 2.5 billion people at risk for infection and an estimated 284-528 million cases annually.

Chikungunya (CHIKV) is a single-stranded mosquito-borne RNA virus that is a member of the Togaviridae family, genus *alphavirus*. The early clinical presentation of CHIKV infection is similar to DENV and it can be difficult to distinguish the two initially. However, extremely painful, debilitating polyarthralgias (pain in multiple joints) and higher fevers are much more typical in CHIKV infections. The joint pain and swelling can last for weeks to months, or even years, thereby negatively impacting the quality of life of people long after the acute disease phase has passed. Although there is no cure or clinically available vaccine for CHIKV, the disease is rarely fatal if well-managed.

Like dengue, chikungunya threatens populations mainly in Africa and Asia, but tends to occur in epidemic outbreaks infecting large populations over discrete spans of time opposed to being a long-standing threat consistently afflicting large numbers of people annually. Almost all documented cases in the US are imported, however in December of 2013, locally-acquired CHIKV infections were reported on the Caribbean island of St. Martin and then in Florida in 2014.

Both dengue (DENV) and chikungunya (CHIKV) viruses are significant global health burdens and are emerging pathogens in the State of Florida and the southern United States. These arboviruses are transmitted to humans by mosquitoes. *Aedes* (*Ae.*) *aegypti* is the principal vector for DENV with *Ae. albopictus* documented as a secondary vector while *Ae. aegypti* and *Ae. albopictus* are the primary vectors for CHIKV. Both of these species of mosquitoes are resident populations in Florida. In 2010, the Florida Department of Health reported that 66 locally-acquired cases of DENV had occurred in Key West, and the first locally-acquired CHIKV cases were confirmed in Florida in July of 2014. Eleven cases of locally-transmitted CHIKV have since been confirmed in Florida counties.

Zika (ZIKV) virus is an emerging mosquito-borne pathogen vectored by *Aedes* (*Ae.*) *aegypti* and *Ae. albopictus*. Large numbers of travel-acquired cases of Zika fever have already been confirmed in the United States, and locally transmitted Zika virus has been confirmed in Florida. With the link strengthening between Zika infection during pregnancy and devastating birth defects, the capabilities of vector mosquito surveillance must be bolstered as it serves as one of the primary means to identify at-risk areas and enact timely preventative measures. Mosquito control districts are accordingly in need of robust surveillance tools capable of detecting targets like ZIKV in real time via simple readouts.

In summary, dengue fever (DENV), chikungunya (CHIKV), and Zika (ZIKV) viruses are emerging mosquito-borne pathogens in the state of Florida vectored by *Aedes* (*Ae.*) *aegypti* and *Ae. Albopictus*. Confirmed locally-acquired cases of dengue, chikungunya, and Zika virus infection over the past five (5) years present a heightened risk for epidemics of these diseases in Florida, as well as in the traditional endemic areas in Africa, Asia and the Caribbean. Therefore, there is a need in the art for a strategy to combat this problem.

The devices and methods disclosed herein address these and other needs.

SUMMARY OF THE INVENTION

Provided herein is a colorimetric, passive (e.g. unpowered) mosquito-borne disease surveillance sensor device that integrates DNA aptamer-gold nanoparticle conjugates (Au-aptamers) that can bind saliva expectorated during mosquito sugar feeding and/or mosquito-borne pathogen proteins. Also provided is a method for field surveillance of insects and pathogens (e.g. mosquitoes and mosquito-borne diseases).

In some aspects, the disclosed sensor device contains detector conjugates that can bind saliva proteins, or pathogen proteins found in the saliva, expectorated during mosquito sugar feeding. For example, the detector conjugates can be species-specific. In other aspects, the detector conjugates are pathogen-specific. In these embodiments, saliva expectorated by the species of mosquito on the device can result in agglomeration of the detector conjugates and development of a color change, such as a colored spot on the device.

For example, disclosed herein is a device comprising:
(a) a payload reservoir comprising an insect attractant and/or insect food source; and
(b) a detector conjugate comprising a gold nanoparticle conjugated to a specific detector molecule that binds specifically to a protein present in the saliva of a specific insect to be detected.

Also disclosed herein is a device comprising:
(a) a payload reservoir comprising an insect attractant or insect food source; and
(b) a detector conjugate comprising a gold nanoparticle conjugated to a specific detector molecule that binds specifically to a pathogen protein present in the saliva of an insect infected by the a pathogen.

Also provided herein is a method for detecting specific insects which may be located in an area which method comprises:

(a) providing in said area a sensor device which comprises: a payload reservoir comprising an insect attractant or insect food source; and a detector conjugate comprising a gold nanoparticle conjugated to a specific detector molecule that binds specifically to a protein present in the saliva of said specific insect to be detected;

(b) allowing said specific insects to alight on or feed on said sensor device under conditions suitable to allow the binding of said protein to said detector conjugate to form an agglomerated detector conjugate; and (c) visualizing or quantitating the binding of said protein to said detector conjugate to form an agglomerated detector conjugate to determine the presence of the protein.

Also provided herein is a method for detecting an insect infected with a pathogen which may be located in an area, the method comprising:

(a) providing in said area a sensor device which comprises: a payload reservoir comprising an insect attractant or insect food source; and a detector conjugate comprising a gold nanoparticle conjugated to a specific detector molecule that binds specifically to a pathogen protein present in the saliva of an insect infected by the a pathogen;

(b) allowing said specific insects to alight on or feed on said sensor device under conditions suitable to allow the binding of said pathogen protein to said detector conjugate to form an agglomerated detector conjugate; and (c) visualizing or quantitating the binding of said pathogen protein to said detector conjugate to form an agglomerated detector conjugate to determine the presence of the pathogen protein.

In some aspects, disclosed herein is a method for detecting specific insects which may be located in an area which method comprises (a) providing in said area a sensor device which comprises a releasing wick, a detector conjugate comprising a gold nanoparticle conjugated to a specific detector molecule that binds specifically to a protein present in the saliva of said specific insect to be detected, and an insect attractant or insect food source; (b) allowing said specific insects to alight on or feed on said sensor device such that said protein binds to said detector conjugate; (c) exposing said bound detector conjugate to a concentration of NaCl of about 1 mM to about 1000 mM NaCl or more specifically 1-100 mM NaCl to agglomerate said bound detector conjugate; and (d) visualizing or quantitating said agglomerated detector conjugate. In a specific embodiment, the agglomerated detector conjugate is visualized or quantified in a NaCl concentration of about 250 mM. The term "about" as used herein refers to the stated amount and ±10% of the stated amount.

In some aspects, the disclosed sensor device contains detector conjugates that can bind pathogen proteins in an insect food source. In these embodiments, digestion of the food source by the mosquito results in agglomeration of the detector conjugates and development of a color change in the mosquito. This food source preferably also contains a toxic substance that kills the mosquito for collection and evaluation. The mosquito can therefore be collected and evaluated for color changes.

For example, provided herein is a method for detecting specific insects which may be located in an area which method comprises:

(a) providing in said area a sensor device which comprises: a payload reservoir comprising an insect attractant or insect food source; a toxic substance (e.g., toxic sugar water substance); and a detector conjugate comprising a gold nanoparticle conjugated to a specific detector molecule that binds specifically to a protein present in the saliva of said specific insect to be detected;

(b) allowing said specific insects to alight on or feed on said sensor device such that said detector conjugate is ingested by the insect, wherein said protein binds to said detector conjugate to form an agglomerated detector conjugate before, during, or after ingestion; and (c) visualizing or quantitating said agglomerated detector conjugate in the insect.

Also provided herein is a method for detecting an insect infected with a pathogen which may be located in an area, the method comprising:

(a) providing in said area a sensor device which comprises: a payload reservoir comprising an insect attractant or insect food source; a toxic substance (e.g., toxic sugar water substance); and a detector conjugate comprising a gold nanoparticle conjugated to a specific detector molecule that binds specifically to a pathogen protein present in the saliva of an insect infected by the a pathogen;

(b) allowing said specific insects to alight on or feed on said sensor device such that said detector conjugate is ingested by the insect, wherein said protein binds to said detector conjugate to form an agglomerated detector conjugate before, during, or after ingestion; and (c) visualizing or quantitating said agglomerated detector conjugate in the insect.

In some embodiments, the insects to be detected are disease vectors carrying a virus, bacterium or parasite which causes disease in mammals, and the protein specific to said insects to be detected is a virus, bacterium or parasite protein. The animal can be a human, a livestock animal, or any mammal.

Examples of diseases to be detected include but are not limited to Dengue fever, Zika fever, chikungunya, Rift Valley fever, yellow fever, malaria, Japanese encephalitis, Saint Louis encephalitis, lymphatic filariasis, West Nile fever, leishmaniasis, sandfly fever, lyme disease, plague, tularaemia, Chagas disease, and onchocerciasis, or any insect-borne disease. Therefore, the proteins to be detected by the sensor devices and methods of the invention preferably include, but are not limited to *P. falciparum* histidine-rich protein 2 (PFHRP2) and lactate dehydrogenase (PFLDH), viral envelope (capsid) or spike proteins/antigens on all viruses, flagellal proteins of bacterial pathogens, salivary proteins listed in table 1 of Z. Peng et al./Insect Biochemistry and Molecular Biology 29 (1999) 909-914, table 1 of E. Orlandi-Pradines et al./Microbes and Infection 9 (2007) 1454-1462, *Anopheles gambiae* salivary protein gSG6. One exemplary protein specific to said insects is mosquito salivary gland allergen Aed a 2.

In some embodiments, the specific detector molecule is aptazyme, apta-beacon, antibody (polyclonal or monoclonal) or a binding fragment thereof. In a specific embodiment, the detector molecule is an aptamer.

Further disclosed herein are methods according to the invention wherein the insect is selected from the group consisting of mosquitoes (*Aedes* spp., *Anopheles* spp., *Culex* spp.), flies, sand flies, tsetse flies, black flies, ticks, lice, midges, fleas, ticks, mites, and triatomine bugs. In some embodiments, the insect is a mosquito, such as those selected from the group consisting of, for example, *Aedes* (*Ae.*) *aegypti, Ae. vexans, Ae. albopictus, Ae. togoi, Ae.* triseriatus, Aedes arabiensis, Culex (Cx.) quinquefasciatus, Cx. pipiens, Cx. tarsalis, Anopheles (An.) sinensis, Anopheles gambiae, and Culiseta (Cs.) inornata.

BRIEF DESCRIPTION OF THE DRAWINGS

The drawings presented herein may not be drawn to scale and any reference to dimensions in the drawings or the following description is specific to the embodiments disclosed. Any variations of these dimensions that will allow the subject invention to function for its intended purpose are considered to be within the scope of the subject invention. Thus, it is understood that these drawings depict only certain specific embodiments of the invention and are not therefore to be considered as limiting in scope. The accompanying figures, which are incorporated in and constitute a part of this specification, illustrate several aspects described below.

DETAILED DESCRIPTION

Figure 1:
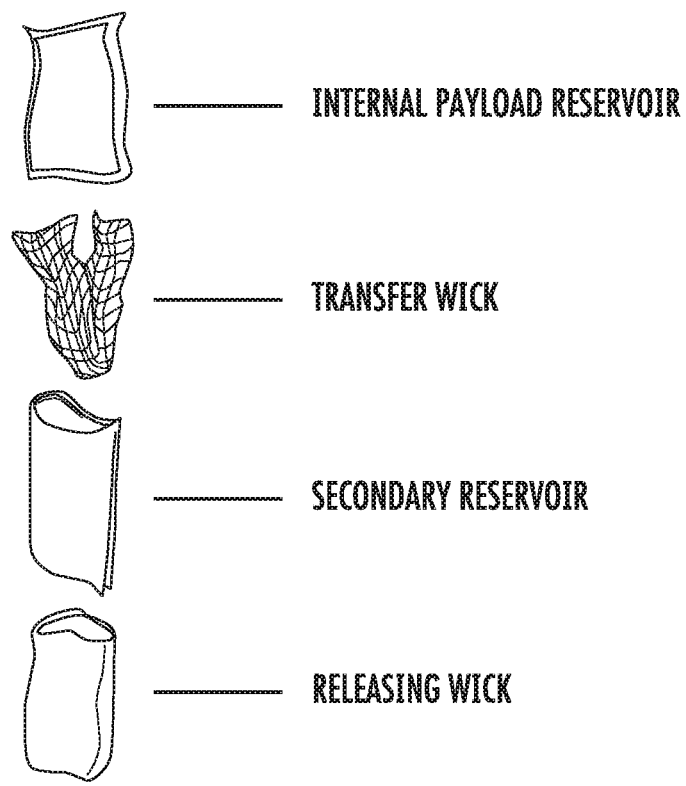
FIG. 1 is a schematic drawing showing a component view of the sensor device, including the wicks.

Provided herein is a colorimetric, passive (e.g. unpowered) mosquito-borne disease surveillance sensor device containing detector conjugates (e.g. DNA aptamer-gold nanoparticle conjugates (Au-aptamers)) that can bind saliva expectorated during mosquito sugar feeding and/or pathogen proteins in mosquitoes after ingestion. Also disclosed are methods for field surveillance of insects and pathogens (for example, mosquitoes and mosquito-borne diseases).

The key to an appropriate defense against these diseases is rapid surveillance of the vector mosquito populations for the viruses. Therefore, a colorimetric sensor device is disclosed to detect and quantitate specific insect feeding activity using detector conjugates (e.g. aptamer-gold nanoparticle conjugates) suitable for field surveillance of mosquito-borne diseases. This surveillance sensor device can be passive (i.e., it requires no power) and can give a colorimetric readout in real-time to detect the presence of vector mosquito species in an area, detect if mosquitoes are infected with a disease of interest, and/or quantify which mosquitoes are infected.

The detector conjugates can be integrated into the device in any manner suitable for mosquito feeding. For example, in some embodiments, the detector conjugates are absorbed in or coated (e.g. dried) on a membrane substrate. In some embodiments, the detector conjugates are contained in a reservoir that is wicked to a surface on the device for mosquito feeding. For example, the device can contain a passive (releasing) wick with no moving parts. See FIGS. 1 and 3 for schematic drawings showing the construction and the operation of an example device. In this design, a payload of a liquid formulation on which mosquitoes will actively feed is sequestered in a reservoir until the device is deployed. Preferably, the reservoir is impermeable until it is deployed by deliberate rupture. At that time, the liquid payload flows into a second reservoir, also preferably impermeable, which has a short, internal transfer wick made of cotton or a similar wicking material protruding from one end. By this wick, the liquid payload is transferred to a second outer wick (releasing wick), that envelopes the device and releases the payload to the surface and into the environment. A photograph of the device is provided in FIG. 2. Devices which are suitable for use in the present methods are described in United States Patent Publication No. 2015-0020439, filed Jul. 16, 2014, the disclosures of which are hereby incorporated by reference in their entirety.

In the present specification, the invention has been described with reference to specific embodiments thereof. However, various modifications and changes may be made thereto without departing from the broader spirit and scope of the invention. The specification and drawings are, accordingly, to be regarded in an illustrative rather than a restrictive sense. The contents of all references cited throughout this application are hereby expressly incorporated by reference as if set forth herein in their entirety. Although specific terms are employed, they are used as in the art unless otherwise indicated.

The description herein discloses embodiments of the invention are particularly useful in the field of mosquito surveillance, however a person with skill in the art will be able to recognize numerous other uses that would be applicable to the devices and methods of the subject invention. While the subject application describes, and many of the terms herein relate to, a use for detecting mosquitoes infected with particular viruses, other modifications apparent to a person with skill in the art and having benefit of the subject disclosure are contemplated to be within the scope of the present invention.

Definitions

In the description that follows, a number of terms are used. In order to provide a clear and consistent understanding of the specification and claims, including the scope to be given such terms, certain definitions follow.

References to "first", "second", and the like (e.g., first and second reservoir), as used herein, and unless otherwise specifically stated, are intended to identify a particular feature of which there can be at least two. Such reference to "first" does not imply that there must be two or more. However, these references are not intended to confer any order in time, structural orientation, or sidedness (e.g., left or right) with respect to a particular feature.

The present invention is more particularly described in the following embodiments and examples that are intended to be illustrative only because numerous modifications and variations therein will be apparent to those skilled in the art. As used in the specification and in the claims, the singular for "a," "an" and "the" include plural referents unless the context clearly dictates otherwise.

Any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. Further, when a particular feature, structure, or characteristic is described in connection with any embodiment, it is within the purview of one skilled in the art to affect such feature, structure, or characteristic in connection with other ones of the embodiments.

The term "insect" as used herein, describes any arthropod species desired to be attracted, monitored, surveilled, quantitated or discovered, in particular, species known as disease-vectoring species. This can include, but is not limited to, mosquitoes, flies, sand flies, tsetse flies, black flies, ticks, lice, midges, fleas, mites, wasps, bees, cockroaches, ants, bedbugs, triatomine bugs, etc. However, the devices of the subject invention can also be utilized with other arthropod or even non-arthropod species. Thus, it should be understood that the term "insect" is used for literary convenience and is not meant to imply any limitation regarding the use of the embodiments of the subject invention.

The terms "feeding solution," "payload," and "indicator" are used herein only for literary convenience to refer to any substance desired to be used to attract, kill, surveil or quantitate insects according to methods of the invention. The embodiments of the subject invention can be used with any suitable substance, which would include those that attract an insect or that in some way cause an insect to make oriented or deliberate movements. The term can also include compounds known to actively control or eradicate insects, so long as such compounds do not interfere with the functions of the devices used with the invention, such as, for example, attracting the insects desired to be detected and quantitated, and the detection method used. Thus, these terms as used herein broadly encompass substances that attract insects, but also include pesticides, including biopesticides, hormones, pheromones, combinations thereof, or any other substance that affects the behavior or biology of an insect. In addition, any of a variety of one or more perfumes, fragrance oils, deodorizers, disinfectants, or other substances desired to be dispersed or volatilized within or around an area are understood to be included under this term.

The term "disease vector" in the context of this invention refers to any agent, such as an insect, that carries and transmits an infectious pathogen into another living organism. Insects are specifically included in this definition. The term "disease" in the context of this invention refers to any infectious pathogen, including but not limited to, a virus, bacterium or parasite.

The term "detector molecule" or "sensor molecule" in the context of this invention refers to any aptamer or antibody (polyclonal or monoclonal) or binding fragment thereof that specifically binds to a compound to be detected. The term includes aptamers, antibodies, and binding fragments thereof that are conjugated to a label of any kind which allows the aptamer, antibody or binding fragment thereof to be visualized or otherwise detected. The term therefore specifically includes gold conjugates of the aptamer, monoclonal antibody or binding fragment thereof. The term "detector conjugate" refers to a detector molecule conjugated to one or more gold nanoparticles.

The term "delivery device," "sensor device" or "device" in the context of this invention refers to a mechanism for providing to insects to be detected an attractant or feeding solution upon which the insect can alight and feed, simultaneously depositing on said device identifiable proteins. The term also includes any such mechanism that includes a detector molecule. Appropriate devices as meant by the term are described in United States Patent Publication No. 2015-0020439, the disclosures of which are hereby incorporated by reference; these devices are included in the meaning of the terms "delivery device," "sensor device" or "device."

The terms "payload," "payload solution," "payload contents" and "feeding solution," refer to a liquid composition to be contained within the device and released to the releasing wick of the device to be made available to insects to be detected. The payload includes control solutions which contain no active ingredient, simple feeding solutions which are designed solely to provide one or more nutrients to the insects, solutions containing detector molecules such as the gold conjugates described herein and solutions containing any additional components such as insect attractants, insect repellants, insecticides, pheromones, preservatives, buffers, surfactants, or any component discernable by a skilled artisan. Any liquid or solution contained or to be contained within the internal payload reservoir is included within the definition of these terms.

The term "internal payload reservoir" or "payload reservoir" refers to any container for enclosing a liquid payload, payload solution, feeding solution, solid payload, or gaseous payload for release or to be made available for feeding or attraction of insects for detection.

"Deployment" in the context of this invention refers to compromising the physical integrity of the internal payload reservoir, to begin operation of the sensor device by allowing the payload to begin transfer to the releasing wick.

The term "insect" in the context of this invention, refers to any of the arthropods that have a chitinous exoskeleton, a three-part body, and three pairs of jointed legs, i.e., any of the members of the Class Insecta. Mosquitoes are specifically included in this definition, including, but not limited to: *Aedes* (*Ae.*) *aegypti, Ae. vexans, Ae. albopictus, Ae. togoi, Ae. triseriatus, Aedes arabiensis, Culex* (*Cx.*) *quinquefasciatus, Cx. pipiens, Cx. tarsalis, Anopheles* (*An.*) *sinensis*, and *Culiseta* (*Cs.*) *inornata*.

Devices

In one aspect, provided herein is a device comprising:

(a) a payload reservoir comprising an insect attractant or insect food source; and (b) a detector conjugate comprising a gold nanoparticle conjugated to a specific detector molecule that binds specifically to a protein present in the saliva of a specific insect to be detected.

In another aspect, disclosed herein is a device comprising:

(a) a payload reservoir comprising an insect attractant or insect food source; and (b) a detector conjugate comprising a gold nanoparticle conjugated to a specific detector molecule that binds specifically to a pathogen protein present in the saliva of an insect infected by the a pathogen.

In another aspect, disclosed herein is a device with a payload reservoir comprising:

(a) an insect attractant and/or insect food source (e.g. sugar water);

(b) a toxic substance lethal to a mosquito; and (b) a detector conjugate comprising a gold nanoparticle conjugated to a specific detector molecule that binds specifically to a pathogen protein (e.g., viral envelope protein).

Therefore, also disclosed is composition comprising an insect food source, a toxic substance, and a detector conjugate that binds specifically to a mosquito-borne pathogen protein.

In one embodiment, the specific detector molecule is an aptamer. In one embodiment, the specific detector molecule is a monoclonal antibody or binding fragment thereof.

In one embodiment, the device further comprises a toxic sugar water substance. In one embodiment, the insect attractant or insect food source is sugar water.

In one embodiment, the specific insect is selected from the group consisting of mosquitoes (*Aedes* spp., *Anopheles* spp., *Culex* spp.), flies, sand flies, tsetse flies, black flies, ticks, lice, midges, fleas, ticks, mites, and triatomine bugs. In one embodiment, the specific insect is a mosquito. In one embodiment, the mosquito is selected from the group consisting of *Aedes* (*Ae.*) *aegypti*, *Ae. vexans*, *Ae. albopictus*, *Ae. togoi*, *Ae. triseriatus*, *Aedes arabiensis*, *Culex* (*Cx.*) *quinquefasciatus*, *Cx. pipiens*, *Cx. tarsalis*, *Anopheles* (*An.*) *sinensis*, *Anopheles gambiae*, and *Culiseta* (*Cs.*) *inornata*.

Figure 2:
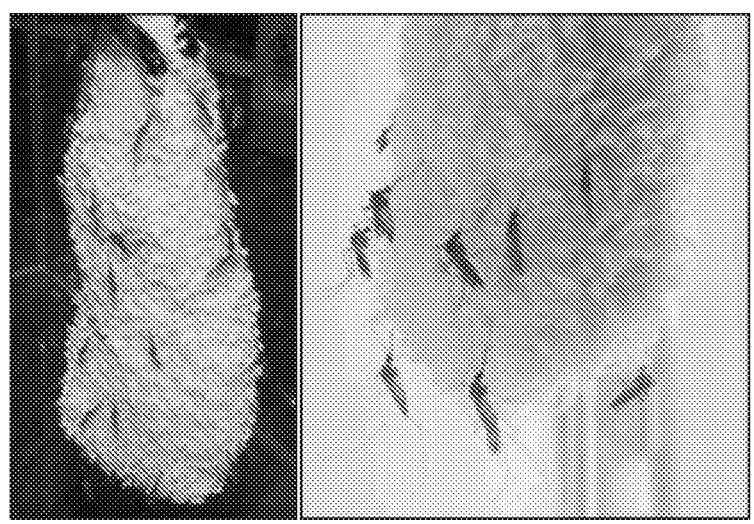
FIG. 2 provides photographs of mosquitoes feeding on sugar-water devices.

In one embodiment, the method is conducted by providing a solution to insects which entices the insects to alight and preferably begin feeding. An exemplary device for this is illustrated in FIG. 1, where at least one internal payload reservoir to hold the payload solution is contained within one or more internal chambers of the device, within the releasing wick. Preferably, this internal payload reservoir is impenetrable by the payload solution or fluid and is sealed, and is designed to maintain its physical integrity until it is deliberately compromised to release the contents. In some embodiments, the internal payload reservoir, or a protective cover for the internal payload reservoir is constructed of a material that is impermeable to at least the target compound, and possibly other chemical, temperature, and environmental conditions. It can also be beneficial with this embodiment for the internal chamber to also be unaffected by mechanical forces that can be applied to the device.

After the payload reservoir is ruptured or otherwise compromised, the payload formulation flows into a secondary reservoir, preferably with a short cotton wick protruding from one end of the reservoir. This first, internal wick (transfer wick) transfers the payload formulation to the final outer wick (releasing wick) that envelops the device and enables release of the payload formulation into the environment, via the secondary reservoir. See FIG. 1.

In some embodiments, the device can comprise of two or more internal payload reservoirs, allowing two or more separate payloads to be carried without mixing until the device is deployed by opening the internal reservoirs. Preferably, in this case, the reservoir or reservoirs are squeezed or punctured to compromise the containers, and then optionally shaken to mix the contents.

In another embodiment, the devices of the subject invention contain a plurality of payload reservoirs that can be sequentially or simultaneously compromised, so as to release target compound in repeated doses over a period of time. This sequential release of target compound can recharge the releasing wick, as the payload solution is depleted.

In one embodiment, the internal payload reservoir is a separate container, capsule, ampoule, or other bulbous vessel, such as illustrated, for example, in FIG. 1, that resides in the secondary reservoir such that, when the delivery device is deformed, the payload reservoir can be physically or mechanically cracked, popped, ruptured, punctured or otherwise damaged or compromised to release compound within the internal payload reservoir. In another particular embodiment, an internal payload reservoir containing target compound is located within an internal chamber within the housing. The internal chamber can be impermeable to chemical, temperature, environmental, or other non-mechanical forms of degradation. Ideally, the internal chamber is also not readily susceptible to being mechanically compromised or opened. A wick can extend out from the impermeable internal chamber. The reservoir within the internal chamber can be mechanically compromised, releasing target compound into the impermeable, uncompromised internal chamber, which contains and isolates the payload contents, which optionally also contains the detector molecule or gold conjugate. The wick can be the mechanism that transmits the target compound from the internal chamber to the external releasing wick, from which it can be dispersed.

The payload reservoir(s) can be constructed of an impermeable, but frangible material that can be popped, ruptured, cracked, broken, ripped, or otherwise mechanically compromised to create at least one opening therein for release of payload compound from the payload reservoir. Alternatively, one or more of the payload reservoirs can be degradable, by methods or techniques described herein. In an alternative embodiment, the internal payload reservoir comprises a material that can be chemically degraded, fragmented, ruptured, dissolved, solvated, or otherwise materially-compromised by methods other than mechanical deforming means. By way of non-limiting example, a reservoir can comprise a gelatin or cellulose material that dissolves or otherwise ruptures when exposed to water or to other substance.

The payload reservoir can be made of a variety of materials, including, but not limited to, glass, ceramics, plastics, nylon, wood, natural fibers or plant products, gelatin, cellulose, hydroxyl methyl cellulose, silicone, polyethylene, aluminized polyethylene, polymers, and/or combinations thereof. Preferably, the material is inert to the gold conjugate compound and does not bind or chemically affect the compound. It is within the skill of a person trained in the art, having benefit of this disclosure, to determine a variety of materials that would be appropriate for the type of reservoir(s) utilized with embodiments of the invention. Such variations that perform the same function, in substantially the same way, with substantially the same results, are within the scope of the subject invention.

The receiving end of a wick can form a seat into which the payload reservoir can be placed. But other configurations or arrangements can be used as well. Ideally, the wick is configured and arranged so that all or most of the available payload solution and gold conjugates can be absorbed by the transfer wick and carried through the wick, eventually to the releasing wick.

In one embodiment, once the transfer wick and payload reservoir have been sealed into the secondary reservoir, the secondary reservoir can be placed into a releasing wick, in the form of a bag or sleeve, made of absorbent, flexible material. The wick can be placed in contact with the releasing wick sleeve material to ensure that the payload solution and the compounds contained therein on the transfer wick is carried to and absorbed by or otherwise distributed through some of, most of, or all of the releasing wick.

In one embodiment, the wick and the external releasing wick are separate components that are in operable contact. For example, the wick and external housing can be placed so that they touch or make contact with each other. By way of further non-limiting example, the delivering end of a wick can actually be attached or connected to the external housing by another device or technique. It can be sewn, clamped, banded, constricted, stapled, adhered, heat sealed, pressure sealed, crimped, melded, molded, or some combination thereof, to the housing. Alternatively, the wick and the external housing can be formed as a single component or article, such that the wick is not required to be additionally connected to the external housing. Some other embodiments comprise a transfer wick that replenishes the secondary reservoir and the releasing wick at a sustained, controlled rate. With these embodiments, the wick can be in contact with the target compound, such that, by capillary action of the wick material, gravity, or other effect, the target compound is transferred to the secondary reservoir or releasing wick for dispersal.

The purpose of the secondary reservoir within the releasing wick is to compartmentalize at least one reservoir, which contains the solution to be released and prevents release of the entire volume of the solution at once. The material of the secondary reservoir can be part of the releasing wick, wherein, for example, the material is fixedly attached or otherwise incorporated as part of the wick, such as in the form of a lining that forms a void within it. Alternatively, the secondary reservoir could be a separate component insertable into the internal housing, such as shown, for example, in FIG. 1.

The secondary reservoir optionally contains and isolates the contents of the deployed payload reservoir from contact with the wick, however, once released, the payload contents can make contact with one or more transfer wicks that extend from the secondary reservoir. In one embodiment, the wick also moves the target compound from the secondary reservoir to the material of the releasing wick. Preferably, a wick also can make sufficient contact with the releasing wick so that the payload fluid can migrate, transfer, leach, or otherwise move from the secondary reservoir to the releasing wick.

Delivery devices can comprise a releasing wick as a mechanism to present a feeding solution containing gold conjugates to insects to be detected. FIG. 1 illustrates an embodiment of the invention where the releasing wick is formed as a sleeve or bag of flexible material into which a secondary reservoir can be placed. The transfer wick can have the receiving end further placed within the secondary reservoir and, if necessary, around or in close proximity to the secondary reservoir. The releasing wick is constructed of a housing or bag of a flexible cloth, paper or similar material capable of rapid absorption and distribution of the payload solution. The releasing wick can be closed but does not have to be closed and can be left open. In some embodiments, the assembled device is placed into a cover or a container.

The releasing wick can be made of any suitable material known in the art which is capable of moving the payload fluid containing gold conjugates, for example, by capillary action, through the wick. This material can include, but is not limited to, any woven or non-woven fabric or fibrous material formed into any of a variety of shapes, weaves, spun products, solid masses, monoliths, other formations and combinations thereof. It may also include natural wood or cellulose products, such as paper or wood board, natural fiber products, such as cotton, linen, flax, bamboo, synthetic microfiber or traditional fiber, nylon, wool, or hemp, as well as ceramics, glass, clay, charcoal, or any combinations thereof, and other materials suitable for use with embodiments of the subject invention which can deliver the payload solution to a surface where insects can feed upon it and deposit the identifiable proteins that allow detection by the gold conjugates present in the solution.

In one embodiment, the wick is made of a fibrous material. In another embodiment, the wick is a sponge or sponge-like material, such as, by way of non-limiting example, an open-cell foam material. However, it is within the skill of a person skilled in the art to determine any of a variety of materials that could be utilized for a wick of the subject invention. Such variations, which provide the same function, in substantially the same way, with substantially the same result, are within the scope of this invention.

In a specific example, the releasing wick can be a cotton-containing terry cloth material or other woven or non-woven cloth material or a sponge or sponge-like material or a paper material, or the like, through which the payload solution containing gold conjugates can migrate or disperse. In one embodiment, the releasing wick is constructed of paper, such as Whatman filter paper 1, or a cotton terrycloth. In another embodiment of the invention, the device comprises an outer latex sleeve, through which insects can feed.

Other embodiments can employ a permeable cover surrounding the external housing as a regulating mechanism to control the rate of diffusion of gold conjugate compound from the external releasing wick. The permeable cover can comprise a material or can have one or more openings that allow diffusion through the permeable cover of the target compound. In one embodiment, material of the permeable cover and/or the number and size of the openings formed within the permeable cover can be modified, depending upon a variety of factors that would be understood to those skilled in the art, so as to control, as near as possible, the release rate or diffusion rate of the payload contents.

With reference to FIG. 1, which shows an example of the delivery device useful for embodiments of the inventive method, the delivery device can comprise an external releasing wick, which can cover the majority of the outside of the device. In another embodiment, the releasing wick can be partially covered by a further material which is impervious to the insects to be detected. The purpose of this optional covering is to limit the area over which the insects can feed, effectively concentrating the feeding to a more limited area and therefore concentrating the collected insect proteins so that they are more easily detected. The optional cover is particularly useful when the insect population is sparse.

A particular Au-aptamer system may not be sensitive enough to produce a perceptible color change when tested against mosquitoes, or (a related issue) that not enough mosquitoes feed on the device and expectorate saliva in a small enough area to induce a color change. Therefore, to bring the mosquitoes to feed on a small area of the device, a cover can be used which exposes only a small, preferably adjustable area to insect feeding. The smaller exposed area of the solution-soaked releasing wick with the Au-aptamers could be severely restricted to facilitate the concentration of expectorated insect saliva in a small area. The number and arrangement of these openings can vary depending upon the size of the external housing, environmental factors, the surface area for feeding that is desired for the scenario in which the device is used, and other factors that would be understood by a person skilled in the art.

The cover also can be configured to activate or deploy the device, for example by comprising a puncturing or breaking device that, when activated, compromises the integrity of the internal payload reservoir. Such covers are contemplated for use with the methods of this invention. While the delivery devices of the subject invention are effective as described above, it can be beneficial or desirable for the devices also to be enclosed within a container. This can ensure that undesirable contact with the contents or the releasing wick is avoided and protects the device until deployment, where the internal payload reservoir is deliberately compromised.

In operation, the internal payload reservoir or reservoirs can be ruptured, punctured, broken, degraded, or otherwise mechanically or chemically compromised, so that the contents are released, slowly or en masse, from the reservoir, prior to or just prior to placing the device in the area to be surveilled for insects. When the payload solution is released from the internal payload reservoir, it flows or migrates towards the walls of the secondary reservoir, so that it can be absorbed into the releasing wick. If more than one internal payload reservoir is used, as the different reservoirs release their contents in sequential intervals, the secondary reservoir is replenished or re-saturated. This continual replenishment or re-saturation can allow the device to be operational for a longer period of time, which may be necessary to detect insects in an area with a sparse population of the insects to be detected.

To detect the presence and quantity of the specific insects that deposit the specific protein which binds to the gold conjugate (to the aptamer or antibody), the conjugate is exposed to high concentrations of salt to facilitate agglomeration of the gold nanoparticles and development of the color change. This may be accomplished by spraying the releasing wick with a solution of NaCl, for example 1 to 1000 mM NaCl, 1 to 100 mM, or most preferably about 250 mM NaCl, and visualized. Alternatively, the detector molecule(s) could be made to fluoresce after interaction with the target molecule and this change could be visualized by shinning a light from a flashlight tuned to a particular wavelength. Also, the color change is largely qualitative (ie., yes or no) as quantitating the change would require other instrumentation.

To reduce the possibility of insufficient aggregation of gold conjugates to produce a visible color change, or the possibility of false positives or false negatives due to fluid flux, diffusion, or evaporation in the device or on the releasing wick, an alternative embodiment employs an attractant payload and separate, clear tubes (e.g., 2 mL tubes) covered with parafilm membrane for saliva collection, essentially forming a two-part device that acts both as a lure and surveillance sensor.

Gold nanoparticles per se are known in the art, and can be prepared according to methods known in the art, such as reduction of $HAuCl_4$. The nanoparticles preferably are about 15 nm in diameter, and are filtered to obtain particles of consistent and homogeneous size. Dynamic light scattering (DLS) and transmission electron microscopy (TEM) can be used to confirm the size and quality of the gold nanoparticles.

In some embodiments, insect proteins or pathogen proteins can be detected using metal nanoparticles (for example, gold nanoparticles) and dynamic light scattering (DLS). See, for example, U.S. Pat. Nos. 8,883,094, 8,026,108, and 9,005,994. DLS can detect particle size change, or size distribution change caused by the formation of nanoparticle dimers, trimers, oligomers, and aggregates. In some embodiments, instead of detecting pathogen proteins, nucleic acid from the insect or the pathogen may be detecting. In some embodiments, the nucleic acid is DNA. In some embodiments, the nucleic acid is RNA. In some embodiments, the method of detecting the nucleic acid involves PCR amplification.

In some embodiments, metal nanoparticles other than gold particles can be used. In additional embodiments, the nanoparticle comprises a transition metal. For example, metals that can be used include gold, silver, cadmium or an alloy thereof.

Aptamers commonly are short sequences of single-stranded nucleic acids, often DNA, that can specifically bind target molecules such as proteins, or other nucleic acids and drugs with antibody-like specificity and affinity. Unlike antibodies, aptamers are created via multiple rounds of a synthetic in vitro selection process called systematic evolution of ligands by exponential enrichment (SELEX) whereby a large initial random library of oligonucleotide sequences is checked for binding to a target. Those sequences that bind are isolated (i.e., selected), amplified by PCR and serve as the pool of oligonucleotides for the next round of selection. This process is repeated until the sequence(s) with the highest specificity and affinity for the target are identified. Large, purified quantities of this newly identified aptamer can then be synthesized entirely in the laboratory using methods known in the art.

Aptamers to specific targets can be generated more rapidly than monoclonal antibodies (several weeks, opposed to months), are stable in a wider range of solutions and temperatures, and can be generated via a completely synthetic process. Aptamers also can be easily conjugated to gold nanoparticles, thereby enabling a colorimetric detection readout for target molecules. The color change indicating whether the target is absent or present is due to the relative aggregation of the gold nanoparticles in solution. When target molecules are not present in solution, gold-aptamers are dispersed and the solution has a particular color. When target molecules are present, aptamers bind to the target(s) thus causing an increase in the aggregation of the gold nanoparticles and result in a change in solution color. High salt conditions also can increase the agglomeration of the gold nanoparticle conjugates. This gold-aptamer approach and closely similar methods have been used recently to develop a colorimetric diagnostic assay for malaria with aptamers specific for the lactate dehydrogenase enzymes of the *Plasmodium* parasite.

Monoclonal antibodies or binding fragments thereof also can be used with the inventive methods in the same way. Persons of skill in the art are well acquainted with methods for their production and use.

Aptamers or monoclonal antibodies suitable for use in the inventive methods are those which specifically bind to any compound present in insects to be detected, and which can be transferred to the releasing wick during feeding so as to be detected by gold conjugate aggregation. Persons of skill in the art are able to discern those useful compounds and to use commonly known methods to produce monoclonal antibodies or aptamers which bind specifically to them. Specific compounds to which the aptamers and/or monoclonal antibodies bind are preferably, but without limitation, selected from the following list: *P. Falciparum* histidine-rich protein 2 (PFHRP2) and lactate dehydrogenase (PFLDH), viral envelope (capsid) or spike proteins/antigens on all viruses, flagellal proteins of bacterial pathogens, salivary proteins listed in table 1 of Z. Peng et al./Insect Biochemistry and Molecular Biology 29 (1999) 909-914, table 1 of E. Orlandi-Pradines et al./Microbes and Infection 9 (2007) 1454-1462, *Anopheles gambiae* salivary protein gSG6. In a specific embodiment, the aptamer binds to Aed a2 protein.

In some embodiments, the target protein is present in the insect saliva. In other embodiments, the target protein is present on the mouthparts or the proboscis of the insect. In still further embodiments, the target protein could be inside the insect as well, for example, in their crop, gut, other tissues, and the like.

Aptamers to mosquito salivary proteins are produced according to methods known in the art. About 100 µg of commercially available recombinant 37 kDa salivary gland allergen Aed a 2 (also sometimes referred to as Protein D7 or Aed a 2) or any other convenient protein for detection can be purchased, collected or purified from insect saliva. Other recombinant proteins are also available, such as 30 kDa salivary gland allergen Aed a 3. Collected whole saliva from *Ae. aegypti* can be used to produce aptamers, for example. Mosquito saliva can be collected from female mosquitoes over about a 1 hour span as known in the art using a small, open 2 mL tube filled with warmed, sterile salt-bicarbonate salivation buffer covered by a thin parafilm membrane through which mosquitoes feed. This method can yield about 500 µg of protein from 250 mosquitoes or about 2 µg of protein per mosquito, per hour of feeding. Alternatively, salivary glands are isolated and saliva is extracted from that tissue and/or saliva is directly collected via the capillary tube-oil method where a glass capillary tube is used with a small amount of oil and is placed around the proboscis and the mosquito is allowed to salivate directly into the oil for 1-2 h. The salivary proteins are then extracted from the oil. From these materials, a small family of high-affinity aptamers, binding specifically to different parts of the target proteins, can be made to facilitate production of multifunctional ligands that have a greater chance of inducing aggregation of the conjugated gold nanoparticles. The aptamers are thiolated to enable coupling to the gold nanoparticles.

Conjugation of the aptamer or monoclonal antibody or binding fragment can be performed by any convenient method known in the art. In one method, an aqueous solution of the gold nanoparticles is incubated with aptamer(s) at an approximate molar ratio of 1:100 nanoparticle:aptamer with agitation for about 24-72 hours, or preferably 48 hours. Afterwards, the solution is brought into 0.1 M NaCl, 10 mM phosphate buffer (pH 7) and allowed to equilibrate for about 48 hours. The resulting gold conjugates then can be separated by any convenient method, such as by centrifugation, and washed with buffer to remove any free (unconjugated) aptamer. Successful conjugation to form an Au-aptamer complex is confirmed using 2.5% agarose gel electrophoresis. The conjugates can be stored under refrigeration until use.

Specific binding of the gold conjugate can be tested prior to use of each batch with any standard binding assay as known in the art. For example, the conjugates can be mixed with the specific protein to which they bind (and to a control protein) in different concentrations, then the salt concentration can be increased to induce agglomeration of bound conjugate. The salt (NaCl) concentration preferably is in the range of 1-1000 mM NaCl, and most preferably is in the range of 1-100 mM NaCl, or is about 250 mM NaCl. The extent of the agglomeration can be detected by colorimetric change.

Alternatively, the detector molecule(s) could be made to fluoresce after interaction with the target molecule. In some embodiments, the target protein can be detected by fluorescent response, phosphorescent response, chemiluminescent response, colorimetric response, infrared detection, ultraviolet (UV) detection, and combinations thereof.

In some embodiments, provided herein are kits for the detecting insect proteins or pathogen proteins comprising: an insect attractant or food source, gold nanoparticles, a specific detector molecule, and optionally, preservative, additive, buffer, negative control sample, positive control sample, packaging material, or instruction for use.

Methods

In one aspect, provided herein is a method for detecting specific insects which may be located in an area which method comprises:

(a) providing in said area a sensor device which comprises: a payload reservoir comprising an insect attractant or insect food source; and a detector conjugate comprising a gold nanoparticle conjugated to a specific detector molecule that binds specifically to a protein present in the saliva of said specific insect to be detected;

(b) allowing said specific insects to alight on or feed on said sensor device under conditions suitable to allow the binding of said protein to said detector conjugate to form an agglomerated detector conjugate; and (c) visualizing or quantitating the binding of said protein to said detector conjugate to form an agglomerated detector conjugate to determine the presence of the protein.

In another aspect, provided herein is a method for detecting an insect infected with a pathogen which may be located in an area, the method comprising:

(a) providing in said area a sensor device which comprises: a payload reservoir comprising an insect attractant or insect food source; and a detector conjugate comprising a gold nanoparticle conjugated to a specific detector molecule that binds specifically to a pathogen protein present in the saliva of an insect infected by the a pathogen;

(b) allowing said specific insects to alight on or feed on said sensor device under conditions suitable to allow the binding of said pathogen protein to said detector conjugate to form an agglomerated detector conjugate; and (c) visualizing or quantitating the binding of said pathogen protein to said detector conjugate to form an agglomerated detector conjugate to determine the presence of the pathogen protein.

In one embodiment, the visualizing or quantitating is a colorimetric change. In one embodiment, the colorimetric change is from red to blue. In an alternative embodiment, the colorimetric change is from blue to red.

In one embodiment, the specific detector molecule is an aptamer. In one embodiment, the specific detector molecule is a monoclonal antibody or binding fragment thereof.

In one embodiment, the device further comprising a toxic sugar water substance. In one embodiment, the insect attractant is sugar water.

In one embodiment, the specific insect is selected from the group consisting of mosquitoes (*Aedes* spp., *Anopheles* spp., *Culex* spp.), flies, sand flies, tsetse flies, black flies, ticks, lice, midges, fleas, ticks, mites, and triatomine bugs. In one embodiment, the specific insect is a mosquito. In one embodiment, the mosquito is selected from the group consisting of *Aedes* (*Ae.*) *aegypti*, *Ae. vexans*, *Ae. albopictus*, *Ae. togoi*, *Ae. triseriatus*, *Aedes arabiensis*, *Culex* (*Cx.*) *quinquefasciatus*, *Cx. pipiens*, *Cx. tarsalis*, *Anopheles* (*An.*) *sinensis*, *Anopheles gambiae*, and *Culiseta* (*Cs.*) *inornata*.

In one embodiment, the presence of the pathogen protein in the insect is detected when the gold nanoparticles aggregate in comparison with a control or a negative sample not containing the pathogen protein where the nanoparticles do not aggregate.

In another aspect, provided herein is a method for detecting specific insects which may be located in an area which method comprises:

(a) providing in said area a sensor device which comprises: a payload reservoir comprising an insect attractant or insect food source; a toxic sugar water substance; and a detector conjugate comprising a gold nanoparticle conjugated to a specific detector molecule that binds specifically to a protein present in the saliva of said specific insect to be detected;

(b) allowing said specific insects to alight on or feed on said sensor device such that said detector conjugate is ingested by the insect, wherein said protein binds to said detector conjugate to form an agglomerated detector conjugate before, during, or after ingestion; and (c) visualizing or quantitating said agglomerated detector conjugate in the insect.

In one aspect, provided herein is a method for detecting an insect infected with a pathogen which may be located in an area, the method comprising:

(a) providing in said area a sensor device which comprises: a payload reservoir comprising an insect attractant or insect food source; a toxic sugar water substance; and a detector conjugate comprising a gold nanoparticle conjugated to a specific detector molecule that binds specifically to a pathogen protein present in the saliva of an insect infected by the a pathogen;

(b) allowing said specific insects to alight on or feed on said sensor device such that said detector conjugate is ingested by the insect, wherein said protein binds to said detector conjugate to form an agglomerated detector conjugate before, during, or after ingestion; and (c) visualizing or quantitating said agglomerated detector conjugate in the insect.

In one embodiment, the visualizing or quantitating is a colorimetric change. In one embodiment, the colorimetric change is from red to blue.

In one embodiment, the specific detector molecule is an aptamer. In one embodiment, the specific detector molecule is a monoclonal antibody or binding fragment thereof.

In one embodiment, the device further comprising a toxic sugar water substance. In one embodiment, the insect attractant is sugar water.

In one embodiment, the specific insect is selected from the group consisting of mosquitoes (*Aedes* spp., *Anopheles* spp., *Culex* spp.), flies, sand flies, tsetse flies, black flies, ticks, lice, midges, fleas, ticks, mites, and triatomine bugs. In one embodiment, the specific insect is a mosquito. In one embodiment, the mosquito is selected from the group consisting of *Aedes* (*Ae.*) *aegypti, Ae. vexans, Ae. albopictus, Ae. togoi, Ae. triseriatus, Aedes arabiensis, Culex* (*Cx.*) *quinquefasciatus, Cx. pipiens, Cx. tarsalis, Anopheles* (*An.*) *sinensis, Anopheles gambiae*, and *Culiseta* (*Cs.*) *inornata*.

In one embodiment, the toxic sugar water substance can include, for example, an essential oil (such as garlic oil), eugenol, pyrethrins, permethrins, pyrethroids, synthetic pyrethroids, and/or organophosphate insecticides. Another example includes Terminix AllClear Mosquito Bait & Kill product.

In some embodiments, the insects to be detected are disease vectors carrying a virus, bacterium or parasite which causes disease in mammals, and the protein specific to said insects to be detected is a virus, bacterium or parasite protein. The animal can be a human, a livestock animal, or any mammal.

Examples of diseases to be detected include but are not limited to Dengue fever, Zika fever, chikungunya, Rift Valley fever, yellow fever, malaria, Japanese encephalitis, Saint Louis encephalitis, lymphatic filariasis, West Nile fever, leishmaniasis, sandfly fever, lyme disease, plague, tularaemia, Chagas disease, and onchocerciasis, or any insect-borne disease. Therefore, the proteins to be detected by the sensor devices and methods of the invention preferably include, but are not limited to *P. falciparum* histidine-rich protein 2 (PFHRP2) and lactate dehydrogenase (PFLDH), viral envelope (capsid) or spike proteins/antigens on all viruses, flagellal proteins of bacterial pathogens, salivary proteins listed in table 1 of Z. Peng et al./Insect Biochemistry and Molecular Biology 29 (1999) 909-914, table 1 of E. Orlandi-Pradines et al./Microbes and Infection 9 (2007) 1454-1462, *Anopheles gambiae* salivary protein gSG6. One exemplary protein specific to said insects is mosquito salivary gland allergen Aed a 2. In some embodiments, the protein specific to said insects is selected from the proteins listed in Table 1.

In some embodiments, the specific detector molecule is aptazyme, apta-beacon, antibody (polyclonal or monoclonal) or a binding fragment thereof. In a specific embodiment, the detector molecule is an aptamer.

The methods of this invention can be used to detect any insects, including insects carrying potential disease-causing organisms and those which are not infected. Preferably, the devices detect and measure, preferably quantitatively or semi-quantitatively, the numbers of mosquitoes or the numbers of infected mosquitoes in an area. Most preferably, the methods detect and measure, preferably quantitatively or semi-quantitatively, the numbers of mosquitoes carrying or infected with a particular disease-causing organism such as DENY, ZIKV, or CHIKV. In one embodiment, the disease causing organism is a *flavivirus*. In one embodiment, the disease causing organism is an arbovirus. In one embodiment, the disease causing organism is Zika virus. In one embodiment, the disease causing organism is dengue virus. In one embodiment, the disease causing organism is chikungunya virus. In one embodiment, the disease causing organism is St. Louis encephalitis virus. Any insect capable of feeding on the sensor device and depositing identifiable protein such as a salivary protein or material from a disease pathogen present in the saliva of an infected insect is contemplated as suitable for the methods of the invention. Insects include, for example, mosquitoes, which can include, *Aedes* (*Ae.*) *aegypti, Ae. vexans, Ae. albopictus, Ae. togoi, Ae. triseriatus, Aedes arabiensis, Culex* (*Cx.*) *quinquefasciatus, Cx. pipiens, Cx. tarsalis, Anopheles* (*An.*) *sinensis, Anopheles gambiae, Culiseta* (*Cs.*) *inornata*, and the like.

In alternative embodiments, the methods can detect arthropods. Many disease-causing organisms are carried by or bred within insects or other arthropods. Insects are any of the large class (Insecta) of small arthropod animals characterized, in the adult state, by division of the body into head, thorax, and abdomen, three pairs of legs on the thorax, and, usually, two pairs of membranous wings; arthropods are any of the largest phylum (Arthropoda) of invertebrate animals with jointed legs, a segmented body, and an exoskeleton, including herein, for example, insects, arachnids such as spiders, mites and ticks.

In use, the proteins which identify a particular insect or group of insects or which identify a particular disease entity (e.g., a virus) can be expectorated or deposited during feeding on or at the releasing wick. These proteins bind specifically to the gold conjugates that impregnate the wick and induce their aggregation in solution to cause a visible color change. In other embodiments, the gold conjugates are ingested by the mosquitoes, which then bind pathogen proteins and agglomerate in the mosquito.

The internal payload reservoir can be filled with practically any liquid formulation, e.g. a volatile mosquito attractant or sugar water, or any solution containing a food source for the insect to be detected. Example payload contents for detection of mosquitoes comprise water and sucrose. Other attractants and food substances contemplated for use with the inventive methods include, but are not limited to glucose, pheromones, odoriferous food (e.g. Limburger cheese), odoriferous refuse, human scents (e.g. sweat and the like) or the formulations listed in Okumu F O, Killeen G F, Ogoma S, Biswaro L, Smallegange R C, et al. (2010) Development and Field Evaluation of a Synthetic Mosquito Lure That Is More Attractive than Humans. PLoS ONE 5(1): e8951. doi:10.1371/journal.pone.0008951, Journal of Medical Entomology, 47(2):274-282. 2010, Journal of the American Mosquito Control Association, 28(2):123-127. 2012.

In some embodiments of the device, a substance can be added which kills the mosquito after the identifying protein is deposited for detection, so that the device can eliminate individual insects after they are detected.

The payload reservoir preferably also contains a detector compound such as the gold-aptamer conjugates described herein, however in other embodiments, the releasing wick has been impregnated with the gold conjugates prior to construction of the device or deployment of the device and release of the payload contents. Therefore, the gold conjugates can be dried onto the entire releasing wick or onto discrete spots on the releasing wick, so that the payload solution does not need to contain gold conjugates, or the gold conjugates can be added directly to the sugar water payload. In some embodiments, the releasing wick may be a paper or polymer substrate. In some embodiments, the gold conjugates can be dried or deposited on the paper or polymer substrate.

The methods and devices of the subject invention are amenable for use in numerous areas where it is desirable to detect, surveil or quantitate insects. The delivery devices can be placed so as to detect insects in a specified area, which can include enclosed or semi-enclosed areas such as rooms, barracks, barns, sheds, stalls, animal enclosures, or vehicles, or open areas in urban, suburban or rural areas such as public parks, farms, animal pens or paddocks, fields, wooded areas, areas near standing water, lakes, areas of disease outbreak or suspected areas of disease outbreak, or any other area where insects reside or are suspected to reside.

REFERENCES

All citations (e.g., scientific journal publications, patents, and other reference material) mentioned herein are hereby incorporated herein by reference in their entirety to the same extent as if each individual citation was specifically and individually indicated to be incorporated by reference.

1. Bhatta et al., Cationic surface reconstructions on cerium oxide nanocrystals: An aberration corrected HRTEM study. ACS NANO, 6(1): 421-430, 2012.
2. Wong et al., Defining the Catalytic Activity of Nanoceria in the P23H-1 Rat, a Photoreceptor Degeneration Model. PLoS ONE 10(3): e0121977, 2015.
3. Das et al., Therapeutic potential of nanoceria in regenerative medicine. MRS BULLETIN, November, 39(11): 976-983, 2014.
4. McCormack et al., Inhibition of Nanoceria's Catalytic Activity due to Ce3+ Site Specific Interaction with Phosphate Ions. J. Phys. Chem. C, 118:18992-19006, 2014.
5. Chen et al., Rare earth nanoparticles prevent Retinal degeneration induced by intracellular peroxides. NATURE Nanotechnology, 1(2):142-150, 2006.
6. Bullivant et al., Materials characterization of feraheme/ferumoxytol and preliminary evaluation of its potential for magnetic fluid hyperthermia. International Journal of Molecular Sciences, 14(9):17501-17510, 2013.
7. Della Rocca et al., A degradable, bioactive, gelatinized alginate hydrogel to improve stem cell/growth factor delivery and facilitate healing after myocardial infarction. Medical Hypotheses, 79(5), 673-7, 2012.
8. Vazquez et al., Polymer-coated cannulas for the reduction of backflow during intraparenchymal infusions. J. Materials Science: Materials in Medicine, 23(8):2037-46, 2012.
9. Willenberg et al., Gelatinized copper-capillary alginate gel functions as an injectable tissue scaffolding system for stem cell transplants. J. Biomaterials Science 22:1621-1637, 2011.
10. Willenberg et al., Self-assembled coppercapillary alginate gel scaffolds with oligochitosan support embryonic stem cell growth. J. Biomedical Materials Research Part A 79A(2): 440-450, 2006.
11. Guzman et al., Dengue: a continuing global threat. Nature Reviews Microbiology 2010:S7-S16.
12. World Wide Web at domain floridahealth of domain category gov, in folder diseases-and-conditions and subfolder dengue in file index.html. Accessed 042115.
13. CDC. Table 1. Laboratory-confirmed chikungunya virus disease cases reported to ArboNET by state. February 2015.
14. WHO. A global brief on vector-borne diseases. Geneva, Switzerland, 2014.
15. Bhatt et al., The global distribution and burden of dengue. Nature 496(7446):504-507, 2013.
16. World Wide Web at domain denguevaccine, domain category org.
17. CDC-U.S. Centers for Disease Control and Prevention. Locally acquired dengue-KeyWest F, 2009-2010. Morb. Mortal. Wkly. Rep. 59:577-581, 2010.
18. Schwartz and Albert, Biology and pathogenesis of chikungunya virus. Nature Reviews Microbiology 8(7): 491-500, 2010.
19. Staples et al., Chikungunya Fever: An Epidemiological Review of a Re-Emerging Infectious Disease. Clinical Infectious Diseases 49(6):942-948, 2009.
20. World Wide Web at domain cdc, domain category gov in folder chikungunya. Accessed 042115.
21. World Wide Web at domain floridahealth, domain category gov in folder diseases-and-conditions and subfolder chikungunya in file index.html. Accessed 042115.
22. Tuerk et al., Systematic evolution of ligands by exponential enrichment: RNA ligands to bacteriophage T4 DNA polymerase. Science 249:505-510, 1990.
23. Ellington and Szostak, In vitro selection of RNA molecules that bind specific ligands. Nature 346:818-822, 1990.
24. Song et al., Aptamers and Their Biological Applications. Sensors 12(1):612-631, 2012.
25. Jeon et al., A colorimetric aptasensor for the diagnosis of malaria based on cationic polymers and gold nanoparticles. Analytical Biochemistry 439(1):11-16, 2013.
26. Lee et al., Cationic Surfactant-Based Colorimetric Detection of *Plasmodium* Lactate Dehydrogenase, a Biomarker for Malaria, Using the Specific DNA Aptamer. Plos One 9(7), 2014.
27. Cheung, Development of aptamer-nanoparticle conjugates as a new approach to malaria diagnosis: University of Hong Kong; 2012.
28. Willenberg et al., United States Patent Publication No. 2015-0020439, 2015.
29. Hall-Mendelin et al., Exploiting mosquito sugar feeding to detect mosquito-borne pathogens. Proc. Natl. Acad. Sci. USA 107(25):11255-11259, 2010.

30. CI W, The role of immunity to mosquito salivary proteins in the pathogenesis of flaviviruses.: Colorado State University; 2007.
31. Owhashi et al., The role of saliva of *Anopheles stephensi* in inflammatory response: identification of a high molecular weight neutrophil chemotactic factor. Parasitology Research 87(5):376-382, 2001.
32. Storhoff et al., One-pot colorimetric differentiation of polynucleotides with single base imperfections using gold nanoparticle probes. J. Am. Chem. Soc. 120(9):1959-1964, 1998.
33. Das et al., The induction of angiogenesis by cerium oxide nanoparticles through the modulation of oxygen in intracellular environments. Biomaterials 33(31):7746-7755, 2012.
34. Agnihotri and Bhide, Design of Aptamer-Gold Nanoparticles Based Colorimetric Assay for the Early Diagnosis of Breast Tumor.
35. Zheng et al., Aptamer-based colorimetric biosensing of dopamine using unmodified gold nanoparticles. Sensors and Actuators B-Chemical 156(1):95-99, 2011.
36. Luo et al., An aptamer-based fluorescence biosensor for multiplex detection using unmodified gold nanoparticles. Chemical Communications 48(51):6387-6389, 2012.
37. Kline et al., Efficacy of three attractant blends tested in combination with carbon dioxide against natural populations of mosquitoes and biting flies at the lower Suwannee wildlife refuge. J. Amer. Mosquito Control Assoc. 28(2):123-127, 2012.
38. Bernier et al., Synergistic attraction of *Aedes aegypti* (L.) to binary blends of L-lactic acid and acetone, dichloromethane, or dimethyl disulfide. J. Medical Entomology 40(5):653-656, 2003.
39. United States Patent Publication No. 2015-0020439.

EXAMPLES

The following are examples that illustrate procedures for practicing the subject invention. The examples are provided for the purpose of illustration only and should not be construed as limiting. Thus, any and all equivalents and variations that become evident as a result of the teachings herein or from the following examples are contemplated to be within the scope of the present invention.

Example 1: Gold Nanoparticle Conjugates

Gold nanoparticles (about 15 nm) are prepared according to methods known in the art. Briefly, aqueous solutions of $HAuCl_4$ (1 mM) are reduced using 38.8 mM sodium citrate. After mixing the reagents, resultant solutions are refluxed for 15-20 minutes and allowed to cool at room temperature. Solutions then are passed through a 0.45 μm syringe filter to obtain nanoparticles with homogenous size. Dynamic light scattering (DLS) and transmission electron microscopy (TEM) are used to confirm the size of the gold nanoparticles. The surface charge of the nanoparticles also is analyzed using dynamic light scattering (DLS).

Aptamers to mosquito salivary proteins are produced according to methods known in the art. About 100 μg of commercially available recombinant 37 kDa salivary gland allergen Aed a 2 (also sometimes referred to as Protein D7 or Aed a 2; MyBioSource, Inc., San Diego, Calif.) and whole saliva collected from *Ae. aegypti* are used to produce aptamers.

Mosquito saliva is collected from at least 250 female mosquitoes over a 1 hour span as known in the art using a small, open 2 mL tube filled with warmed, sterile salt-bicarbonate salivation buffer covered by a thin parafilm membrane through which mosquitoes feed. This method yields about 500 μg of protein from 250 mosquitoes or about 2 μg of protein per mosquito, per hour of feeding. From these materials a small family of high affinity aptamers binding specifically to different parts of the target proteins is made to facilitate production of multifunctional ligands that have a greater chance of inducing aggregation of the conjugated gold nanoparticles. The aptamers are then thiolated to enable coupling to the gold nanoparticles.

Aqueous solutions of the gold nanoparticles are incubated with aptamer(s) specific to mosquito salivary protein(s) or viral proteins, (nanoparticle:aptamer molar ratio 1:100) while rocking for 48 hours. The solutions then are brought into 0.1 M NaCl, 10 mM phosphate buffer (pH 7) and allowed to equilibrate for 48 hours. The resulting gold conjugates then are separated via centrifugation. The collected pellet is washed with 0.1 M NaCl, 10 mM phosphate buffer (pH 7) to remove any free (unconjugated) aptamer. Aliquots are stored at 4° C. until use. Successful conjugation to form an Au-aptamer complex is confirmed using 2.5% agarose gel electrophoresis.

Gold conjugates, (e.g., Au-aptamers) are tested in a tube visually and using UV-Vis spectroscopy in the presence of the specific proteins used to produce the aptamers, e.g. A e 2 protein and/or whole mosquito saliva. Briefly, different concentrations of the target (1 to 100 ng protein(s) or saliva) are incubated with 200 μL of gold conjugate (Au-aptamers; 10 ng to 100 ng) for 10-15 minutes.

The salt concentration then is increased by adding 50-100 μL of 0.25 M NaCl solution. In the presence of high salt concentrations (over about 10 mM NaCl]) and the specific target binding protein(s), the gold conjugates agglomerate. The extent of the agglomeration can be detected by colorimetric change. To check for off-target, non-specific aptamer binding, a control solution containing only a protein (e.g., albumin and/or a complex protein solution such as plasma) also is tested with the gold conjugates by the same methods.

To test the sensitivity of the sensor, a series of spots (about 4 mm diameter) of the gold conjugates (Au-aptamer) are prepared on the Whatman filter paper 1 and allowed to dry. Serial dilutions of the target insect or disease protein are added to the spots and incubated for 15 minutes, then developed in a high concentration salt solution. The visual appearance and high resolution images are acquired, and the sensitivity of the gold conjugate sensor analyzed. The parameters (amount of Au-aptamers applied, spot size, incubation time and developer/salt concentration) can be adjusted to obtain a visible difference when testing target protein(s) applied to sugar-soaked filter paper to mimic conditions of an anticipated field experiment.

Different concentrations of the feeding solution (sugar) also can be tested by directly soaking the filter paper or other material to be used for the releasing wick, to discern the best conditions for achieving sensitive detection. In conditions where the detection is low, such as where the insect population is sparse, or if sensitivity of the colorimetric detection is low, fluorescence conjugated aptamers can be used as an alternative approach to increase the sensitivity of the proposed sensor.

Example 2: Mosquitoes Approach and Actively Feed on Surveillance Devices

Mosquito surveillance devices as depicted in FIG. 1, containing a payload of sucrose in water (control) were deployed and tested in a laboratory setting. Mosquitoes approached and actively fed on the devices. See FIG. 2. This demonstrates that the methods of the invention can be used to detect insects. By adding Au-aptamers targeting mosquito pathogen proteins to the sugar water payload of our devices, infected mosquitoes feeding on the device can cause a local color change from red to blue on the device and the abdomens of these mosquitoes are also rendered blue from the transfer of the Au-aptamers. Correspondingly, uninfected mosquitoes sugar feeding from the device produce no local color changes and their abdomens are red colored because the aggregation of the Au-aptamer nanoparticles is not increased. Hence, by pairing sugar-water+Au-aptamer devices together with attractant-releasing devices in traps along with adding a poison to the sugar water payload (e.g. eugenol), vector mosquito populations can be simultaneously captured and those with disease can be diagnosed and quantified simply by visual inspection. The mosquito surveillance in this Example is shown in FIG. 3.

Furthermore, volatile attractant blends preferentially targeting either *Aedes* or *Anopheles* species, carries of DENY, CHIKV, and ZIKV or malaria respectively, have also been previously described (Kline, D. L., *J Am Mosq Control Assoc*, 28(2):123-127. 2012; Wolfgang, R. et al., *J Chem Ecol*, 2012; 38:235-244). Because the attract-diagnose-kill traps are totally unpowered and require no external supplies, key human populations should have no barriers to adopting and using the technology.

Figure 3:
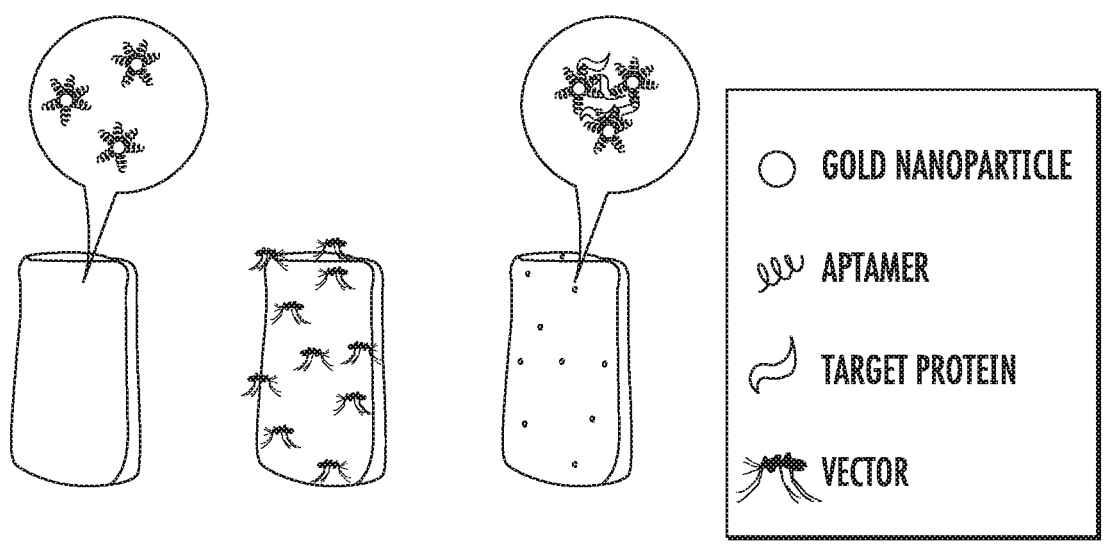
FIG. 3 is a schematic drawing of a sugar-water-gold aptamer sensor device in operation.
Figure 4:
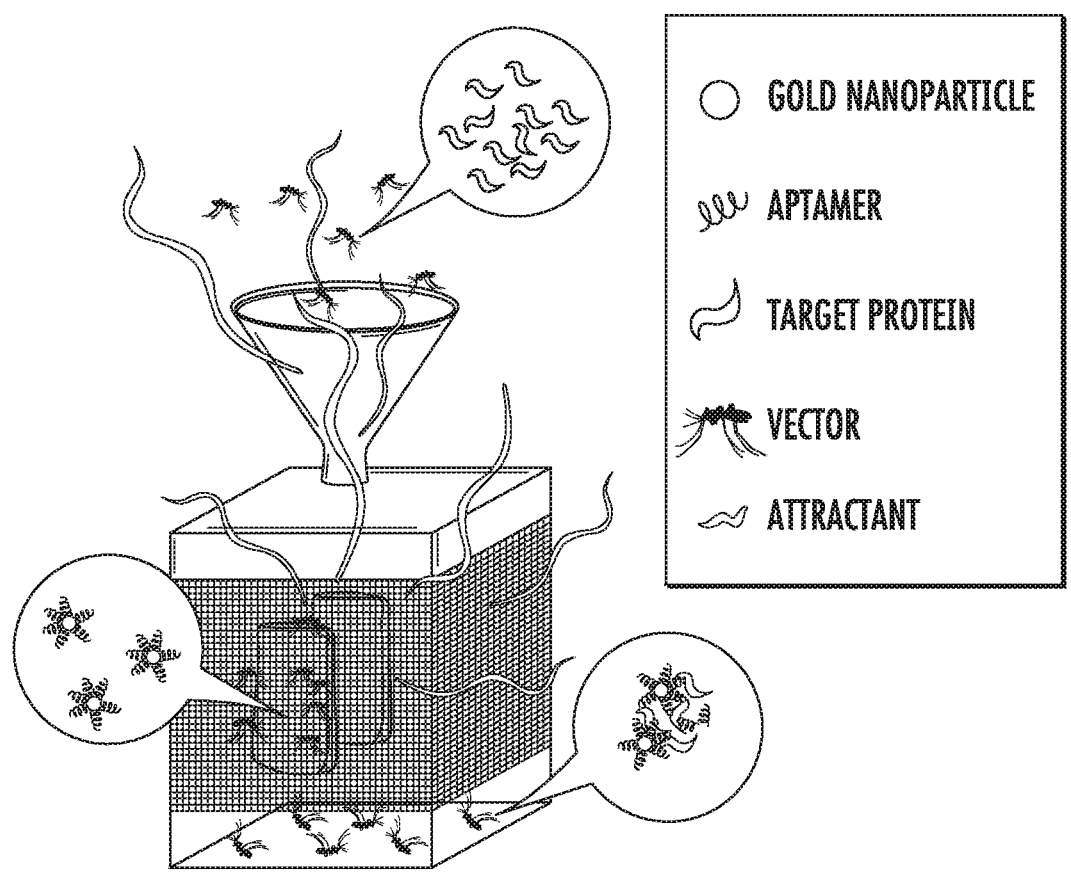
FIG. 4 is a schematic drawing of an attract-diagnose-kill mosquito surveillance trap.

The traps in FIG. 3 are tested using an *Aedes* attractant formulation which is paired with a toxic sugar water substance (device) containing Au-aptamer nanoparticles against CHIKV. The traps are placed in small and large laboratory enclosures with lab-reared mosquitoes, a proportion of which are infected with CHIKV. After 24 h, the traps are collected and the numbers of live and dead mosquitoes counted; the fraction of the dead mosquitoes with blue abdomens is determined. The sugar-feeding device is imaged to quantify the number of blue spots present on the releasing wick due to the aggregation of the Au-aptamer nanoparticles by CHIKV in the saliva expectorated by the mosquitoes during sugar feeding.

Example 3: Deployment of Insect Surveillance Devices

A sensor device is deployed (i.e., squeezed to rupture the internal payload reservoir) and hung singly in the center of each of five small screened boxes. Two hundred and fifty female *Ae. aegypti* mosquitoes then are introduced to each box and allowed to feed on the device for 4 hours. This series of five (5) deployments is repeated at least three independent times. Images are captured at regular intervals to quantitate data such as (1) the average number of mosquitoes feeding on the device at one time, (2) any observable color change anywhere on the device, its location and extent, (3) the intensity of any color change(s) and (4) how long the change lasted. Once the four-hour feeding period is concluded, devices are removed and sprayed with a concentrated NaCl solution (1-1000 mM) to develop color or more intense color.

Example 4: Surveillance of Mosquitoes

Sensor delivery devices with aptamers developed against *Ae. aegypti* salivary proteins, as described and discussed above, are deployed under controlled conditions at the United States Department of Agriculture campus in Gainesville, Fla., in large cages (a semi-field study). Four devices are deployed and hung about 1.5 m from the ground, equidistant from the center and all sides of the enclosure. One thousand female *Ae. aegypti* mosquitoes then are introduced and allowed to feed on the device for 4 hours. Imaging at regular intervals and development with sodium chloride solution for data collection are repeated as for Example 3 to quantitate variables such as those outlined above. The configuration is rotated to an identical cage in a different location on the campus to control for positional effects, and the test repeated. One test consists of a pair of repetitions in at least two different cages. At least three (3) independent tests for each condition are conducted.

Example 5: Detection of Zika Virus

Zika (ZIKV) virus is an emerging mosquito-borne pathogen vectored by *Aedes* (*Ae.*) *aegypti* and *Ae. albopictus*. Large numbers of travel-acquired cases of Zika fever have already been confirmed in the United States, and locally transmitted Zika virus has been confirmed in Florida. With the link strengthening between Zika infection during pregnancy and devastating birth defects, the capabilities of vector mosquito surveillance must be bolstered as it serves as one of the primary means to identify at-risk areas and enact timely preventative measures. Mosquito control districts are accordingly in need of robust surveillance tools capable of detecting targets like ZIKV in real time via simple readouts.

As a first step, aptamers are designed to bind target proteins and closely homologous non-target proteins (non-target for negative selection to prevent cross-reactivity). Target proteins include ZIKV envelope protein. Therefore, aptamers can be generated against isolated or recombinant ZIKV envelope protein or ZIKV whole-virus lysates.

Aptamers can also be designed to bind salivary proteins specific for target vector species. Therefore, 50 μg of salivary proteins from whole saliva and salivary glands are collected from female *Ae. albopictus* and *aegypti* respectively. Whole saliva is collected from 2500 female mosquitoes using the glass capillary-immersion oil method and salivary glands are isolated from 250 females. Isolated salivary gland pairs (10-20) are suspended in pH 7.4 bicarbonate-buffered saline (1 μL/gland pair) and subjected to either a brief (10 s) sonication or dissociation using a Miltenyi gentle MACS™ system with C Tubes and the liquid fractions collected. The whole-saliva collections and salivary gland liquid fractions undergo a trichloroacetic acid (TCA) precipitation protocol to purify and concentrate the salivary proteins. These proteins are resolubilized in bicarbonate-buffered saline; small fractions are run on a protein gel (silver stain) for compositional analysis and the remainder shipped to BPB.

Target-specific aptamers are produced using multiplex SELEX process where aptamers for each different target can be generated simultaneously. Not only does the multiplexed version of SELEX save a considerable amount of time and expense, it also helps reduce cross-reactivity by using non-targets in the process. The multiplexed SELEX ensures that the generated aptamers specific for ZIKV or *Ae. albopictus* salivary proteins do not cross-react with other Flaviviruses (e.g., DENV) or *Ae. aegypti* proteins, respectively. Furthermore, families of aptamers are used for each intended target, ensuring multiple aptamers bind multiple sites on the same target protein. This strategy produces a robust amount of aptamer-target binding. When the aptamers are conjugated to AuNPs (Au-aptamers), this robust target binding facilitates the intended color change by promoting Au-aptamer aggregation.

AuNPs (~13 nm) are prepared as described (Storhoff J J, et al. One-pot colorimetric differentiation of polynucleotides with single base imperfections using gold nanoparticle probes. J Am Chem Soc 1998:120; 9. p 1959-64.). Briefly, aqueous solutions of $HAuCl_4$ (1 mM) are reduced using sodium citrate (38.8 mM). After mixing the reagents, resultant solutions are refluxed for 15-20 min and allowed to cool at room temperature. Then solutions are passed through a 0.45 μm syringe filter to obtain nanoparticles with homogenous size. Dynamic light scattering (DLS) and transmission electron microscopy (TEM) are used to size the nanoparticles. Surface charge of the nanoparticles is analyzed using Zeta potential measurements.

Aqueous solutions of AuNPs are incubated with thiolated target-specific aptamer(s) (NPs:aptamer molar ratio 1:200) while rocking for 24 h. The solutions are washed two times with 1 mM Tris-HCl (pH 7.4) with 0.1 mM $MgCl_2$ and finally resuspended to 10 mM Tris-HCl (pH 7.4) with 1 mM $MgCl_2$. These Au-aptamer solutions are stored at 4° C. until use.

Au-aptamer target binding and subsequent aggregation-induced solution color change is analyzed in a tube visually and with UV-Vis spectroscopy. Briefly, different concentrations of the protein targets (1 to 100 ng) are incubated with 25 μl of Au-aptamers for 10-15 min. Next, 10 μl of 2M NaCl concentration are added to enhance aggregation. In presence of high salt concentration and target protein(s), Au-aptamers aggregate and the extent of aggregation can be detected by colorimetric change[42]. To check for off-target, non-specific aptamer binding, a solution containing non-target protein(s) is tested with the Au-aptamers as described above.

To fabricate devices, Whatman® filter paper #1 or terrycloth is used for releasing wicks. Different concentrations of Au-aptamers are added to the payload solution (i.e., 10% sucrose) and deploy (squeeze) the devices. Ranges of target protein concentrations are then added onto the wick; visual appearance and high-resolution images is assessed to analyze the sensitivity of the sensor. Parameters such as incubation time and developer/salt concentration can be adjusted to increase performance.

Testing of the salivary surveillance tools/sensor is conducted at the USDA facilities and a laboratory mosquito colony. The sensor devices are deployed (squeezed) and hung singly in the center of a small screened box. Female *Ae. albopictus* (250) are introduced and allowed to feed on the device for 4 h. Images are captured at regular intervals to quantify data such as the average number of mosquitoes feeding from a device at any one time, the degree of color change on the device (if so, how many spots), the intensity of color change(s) and how long the color change lasted. After the feeding period, the devices are sprayed with a 2M NaCl solution to obverse if color-changed spots appear or if present ones further develop. A semi-field study is conducted in the large cages. For these tests, devices are deployed and hung 1.5 m from the ground, equidistant from the center and all sides. Female *Ae. albopictus* (1000) are introduced and allowed to feed for 4 h. Variables like those outlined above are quantitated from images taken at regular intervals, and NaCl developer is applied to the devices after the feeding period.

Testing of the ZIKV tools and sensors occurs in a laboratory. In this Example, expectorated saliva is inspected, and also mosquitoes consume Au-aptamer solutions to visualize their midguts for ZIKV infection. As such, ATP or an ATP analog is included in the sucrose-Au-aptamer solutions to activate purinergic receptors on the tarsi, labral and cibarial sensilla. This activation routes the bulk of sucrose-Au-aptamer solutions to the midgut instead of the crop where the bulk of ingested sugar solutions would normally be shuttled and stored.

In vitro serial-dilution titer assays with intact ZIKV and DENV 1-4 are conducted to determine specificity, sensitivity and limits of detection of the Au-aptamers. Alto recently received from the CDC a low passage isolate of ZIKV from Puerto Rico (strain PRVABC59) which originated from human serum in December 2015. This strain of ZIKV was used because it is responsible for the epidemic in the Americas (December 2015-present) and it is a risk for importation to Florida. Alto also has access to the following dengue viruses at the FMEL from the CDC: dengue-1 (Hawaii, TC00835), dengue-2 (New Guinea C, M29898), dengue-3 (H-87, TC00881), and dengue-4 (H-241, TC00594). ZIKV and DENV 1-4 are cultured using African green monkey (Vero) cells using standard procedures. Viral titers (as plaque forming units (PFUs)/mL) of prepared stocks are determined by plaque assays in Vero cells and real-time, quantitative PCR (qPCR) using established methods. Solutions with viruses starting at titers of $10^7$ PFU/mL and are serial-diluted in 10-fold steps into 7 solutions for each virus. ZIKV Au-aptamers at the optimal concentration(s) determined from previous experiments are combined with the serial-diluted virus solutions (total volume=200 μl) to determine the colorimetric response of the Au-aptamers solutions (UV-Vis) and the minimal ZIKV titer detectable colorimetrically by eye.

Example 6. Mosquito Saliva Collection

Mosquito saliva collection was conducted using the parafilm covered microcentrifuge tubes filled with sodium bicarbonate-buffered saline and lambskin membranes filled with 10% sugar (sucrose) water. *Aedes aegypti* and *Aedes albopictus* mosquitoes were used for these tests. Both watered and water-deprived (16 h) mosquitoes from both groups were tested. Protein was quantified. It is clear from the salivary protein amounts that the lambskin membrane collectors with sugar water performed well. However, the presence of the dye in the collectors could have confounded the protein quantification assay and will also likely interfere with the downstream development of aptamers to the salivary proteins.

Another round of saliva collection from *Ae. aegypti* using collectors made from narrow sausage casing filled with sugar water to reduce the total volume in the collector to hopefully increase the overall collected salivary protein concentration. The collection procedure was improved in this second round via the inclusion of a blank collector. This blend was exactly the same sugar water-filled sausage casing collector placed in a cage with no mosquitoes for the same amount of time as the collectors placed into cages with mosquitoes. This addition allows for subtraction of any background signal or signal from proteins coming from the casing/membrane. Undyed sugar water was also used to remove any chance of interference with the protein quantification assay from the dye. Though the mosquitoes were clearly interested in these smaller sausage-casing feeders, the protein quantification results indicated that lower protein concentrations were achieved.

Example 7. Production of Gold Nanoparticles

Analytic detection with gold Nanoparticles (AuNPs)-aptamer is based on surface plasmon resonance (SPR) and absorption bands which are extremely sensitive to the size as well as aggregation state of the nanoparticles. It is therefore, very important to determine the size of AuNPs such that in the presence of an analyte, the maximum shift is obtained. AuNPs with two different sizes (AuNP1 and AuNP2) were selected for this project.

Figure 5A:
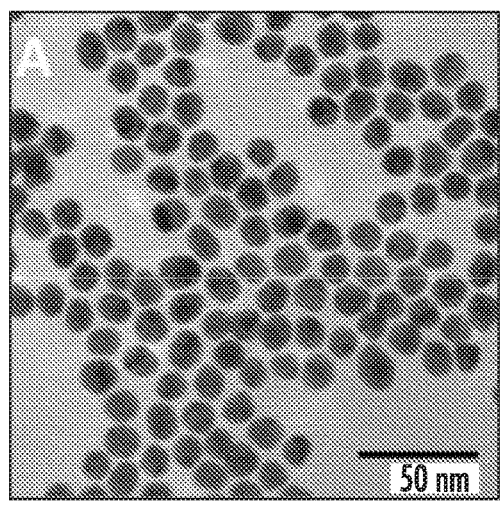
FIG. 5 shows the characterization of the size and optical characteristics of AuNPs. (A) High-resolution transmission electron microscopy (HRTEM) analysis of AuNPs for 15 nm (scale bar 50 nm). (B) HRTEM analysis of AuNPs for 30 nm (scale bar 50 nm). (C) DLS data show the distribution of AuNPs with mean size of 20.10±0.09 nm. (D) DLS data show the distribution of AuNPs with mean size of 36.48±0.2 nm. (E) AuNPs suspensions show red color for both 15 nm and 30 nm. (F) UV-Visible absorption spectra are showing shift from 518 nm to 520 nm.
Figure 5B:
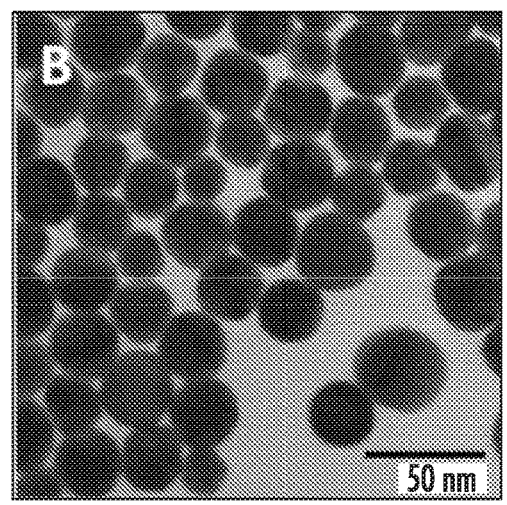
Figure 5C:
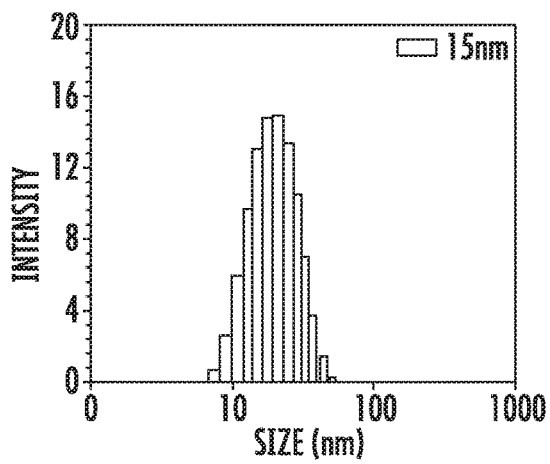
Figure 5D:
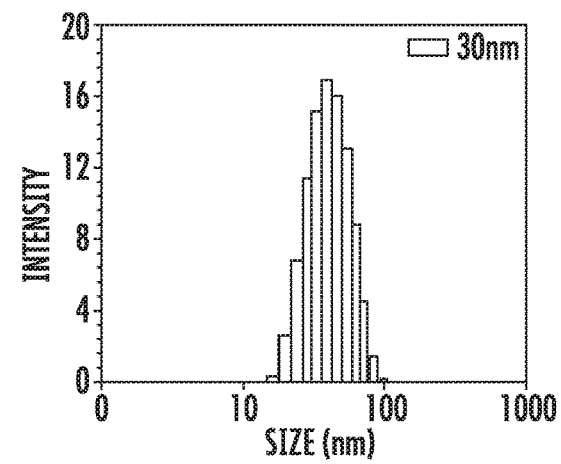
Figure 5E:
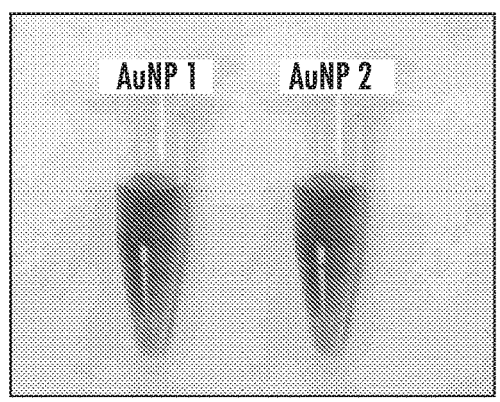
Figure 5F:
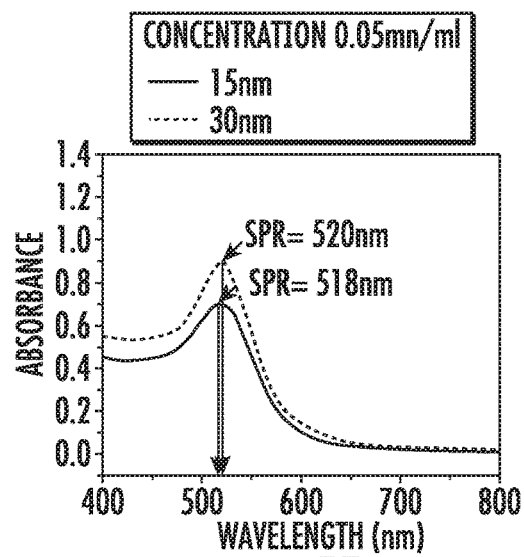
Figure 6A:
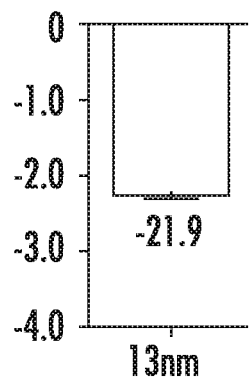
FIG. 6 shows the characterization of 13 nm AuNPs. (A) Zeta Potential measurement, (B) UV-Visible absorbance, (C) DLS analysis and (D) TEM analysis.
Figure 6B:
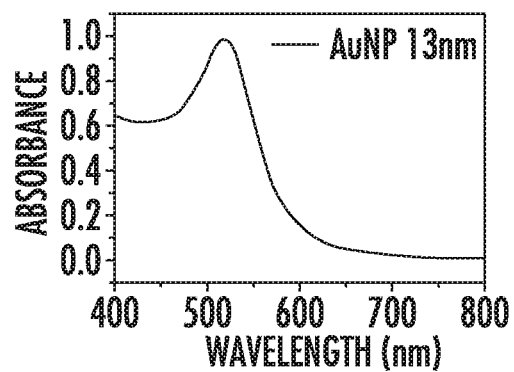
Figure 6C:
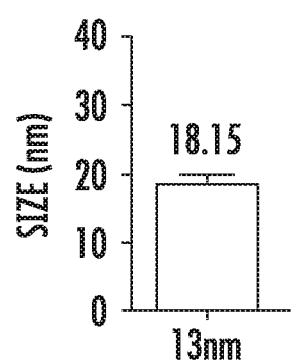
Figure 6D:
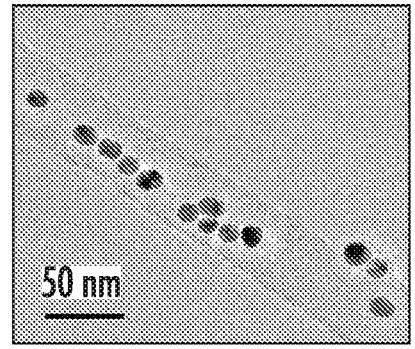

High-resolution transmission electron microscopy (HR-TEM) images of the nanoparticles are shown in FIGS. 5A & 5B. HRTEM images revealed that particles are round in shape and average sizes are on the order of 15 for AuNP 1 and 30 nm for AuNP 2. In addition to the HRTEM analysis, dynamic light scattering (Zetasizer, Malvern Instrument) was used to determine hydrodynamic size and the extent of agglomeration of the AuNPs in aqueous solution (FIGS. 5C & 5D). Histogram data clearly indicate that both the particles are in narrow size ranges (AuNP 1-20.10±0.09 nm & AuNP 2-36.48±0.2 nm) and have very minimal or no agglomeration. FIG. 5E shows suspensions of both the particles are red in color. The advantage of using these specific size particles is that after aggregation, the change in the color of the solution will be maximum (red to red-purple to blue). UV-Vis spectroscopy (Perkin Elmer Lmabda-750S) was used to determine dependence of surface plasmon resonance with the size of nanoparticles. In particular, absorption spectroscopy was performed at room temperature in the range of 400 nm-800 nm. UV-Vis spectroscopy data show that higher particle size results in red-shift in the absorption band (FIG. 5F). The peak shifted from 518 nm to 520 nm with increasing the size from 15 nm (AuNP 1) to 30 nm (AuNP 2). This shift is mainly due to quantum confinement effect which is directly correlated with the size of the particles.

In addition to the size and optical properties, determination of surface charge and functional group present on the surface of the nanoparticles are very important as interaction of aptamers and AuNP depends on the surface properties. Surface charge measurements shown that both the nanoparticles were negatively charged −28.23 mV (AuNP 1) and −30.13 mV (AuNP2). Fourier transform infrared spectroscopy (FTIR; PerkinElmer F-7000) data showed presence of strong peaks at ~3424 cm-1, ~1633 cm-1 and a weak peak at 2923 cm-1 representing the —OH (stretching), —C═O stretching) and —CH stretching respectively. Negative surface charge and FTIR peaks were due to presence of citrate on the surface of the AuNP. The absence of other peaks indicates that there are no unwanted molecules (other than citrate) present on the surface of the AuNPs.

Example 8. Capillary Tube-Immersion Oil Method

In the capillary tube-immersion oil method, mosquitoes are first cold anesthetized and all their wings and legs are removed; then they are stuck down in rows on double-sided tape. Once immobilized, each individual proboscis is placed into glass capillary with a small volume of immersion oil and the mosquito allowed to salivate into the oil for at least 1 h. The method is highly effective for collecting essentially pure saliva/excreted salivary proteins (especially when followed by TCA protein precipitation) but is extremely labor intensive and time consuming. Given that each mosquito maximal excretes less than 1 μL of saliva containing no more than ~20 ng collections from thousands of mosquitoes are required to collect the 10's of ms required for aptamer generation.

In addition to saliva collection, 100 μg of recombinant D7 *Ae. aegypti* salivary protein (MyBioSource, Inc.) as a parallel target for aptamer generation.

The initial comparative compositional analysis is shown in Table 1.

TABLE 1

*Aedes aegypti* Salivary Proteins

| Marker | Protein | MW kDa | Observed kDa | Reference |
|---|---|---|---|---|
| 1 | SGS1 | 345 | 270-400 | {2007, Ribeiro}, {2007, Orlandi-Pradines} |
| 2 | SG4 and SG5 | 260 | 240 | {2011, King} |
| 3 | Unknown protein | 198 | | |
| 4 | Unknown protein | 196 | | |
| 5 | Pyruvate carboxylase | 132 | 125-135 | {2007, Ribeiro} |
| 6 | α-Amylase I | 81 | 75-90 | {2007, Ribeiro} |
| 7 | heat shock cognate 70 protein | 71.4 | 65-71 | {2007, Ribeiro} |
| | Polyadenylate-binding protein | 69.7 | | {2007, Ribeiro} |
| | Salivary apyrase (Aed a 1) | 68 | | {1995, Champagne}, {2012 Machain Williams}, {2007, Orlandi-Pradines}, {2007, Ribeiro}, {2015, Oktarianti} |
| | α-Glucosidase | 67 | | {2007, Ribeiro}, |
| | Esterase 65 kDa | 65 | | {2007, Ribeiro} |
| 8 | Malic enzyme | 63.5 | 62-64 | {2007, Ribeiro} |
| | Salivary apyrase | 63 | | {2015, Oktarianti} |
| | Salivary mucin | 62.3 | | {2007, Ribeiro} |
| 9 | 5'Nucleodase | 61 | 59-60 | {2007, Ribeiro} |
| | Double serine protease | 61 | | {2007, Ribeiro} |
| | Putative adenosine deaminase | 60.6 | | {2007, Ribeiro} |
| | F0F1-type ATP synthase-alpha subunit | 59.4 | | {2007, Ribeiro} |
| | UDP-glucuronsosyl and glucosyl transferase | 59.4 | | {2007, Ribeiro} |
| 10 | Membrane glycoprotein LIG-1 | 58.5 | 54-59 | {2007, Ribeiro} |
| 11 | Serpin (Salivary serpin anti-FXA) | 47 | 45 | {2015, Oktarianti}, {2007, Orlandi-Pradines} |
| | SG1-like 2 | 45 | | {2007, Ribeiro} |
| | Aed a X1 | 44 | | {2007, Ribeiro} |

TABLE 1-continued

*Aedes aegypti* Salivary Proteins

| Marker | Protein | MW kDa | Observed kDa | Reference |
|---|---|---|---|---|
| 12 | D7 | 37-39 | 38-42 | {2007, Ribeiro}, {2015, Oktarianti}, {2007, Orlandi-Pradines}, {2015, Cime-Castillo} |
|  | Serine protease | 39.6 |  | {2007, Ribeiro} |
|  | Adenosine kinase | 38.1 |  | {2007, Ribeiro} |
|  | Salivary purine nucleosidase | 37.9 |  | {2007, Ribeiro} |
| 13 | Trypsin-like salivary secreted protein | 36.8 | 36 | {2007, Ribeiro} |
|  | β3-glucuronyltransferase-1 | 36.7 |  | {2007, Ribeiro} |
| 14 | Salivary gland allergens | 30-33 | 33 | {2015, Cime-Castillo}, {2007, Ribeiro} |
|  | Angiopoietin-like protein variant (fragment) | 33.4 |  | {2007, Ribeiro} |
| 15 | Salivary mucins |  | 17-28 | {2007, Ribeiro} |
|  | Salivary gland allergen-like proteins |  |  | {2007, Ribeiro} |
|  | D7 related proteins |  |  | {2007, Ribeiro}, {2015, Cime-Castillo} |
| 16 | D7 related 1,2,3 protein | 15 | 15 | {2007, Ribeiro}, |
|  | Hypothetical protein-5'nuclease family | 15 |  | {2007, Ribeiro} |
|  | Salivary gland allergen-like proteins |  |  | {2007, Ribeiro} |
| 17 | Glycine rich salivary secreted peptide | 10.8 | 10 | {2007, Ribeiro} |
|  | Protein translocation complex beta subunit | 10.3 |  | {2015, Cime-Castillo} |
|  | Salivary vasodilatory protein precursor | 9.5 |  | {2007, Ribeiro} |
|  | ATP syntase E chain | 9.2 |  | {2007, Ribeiro} |

Example 9. Characterization of Gold Nanoparticles

Figure 7A:
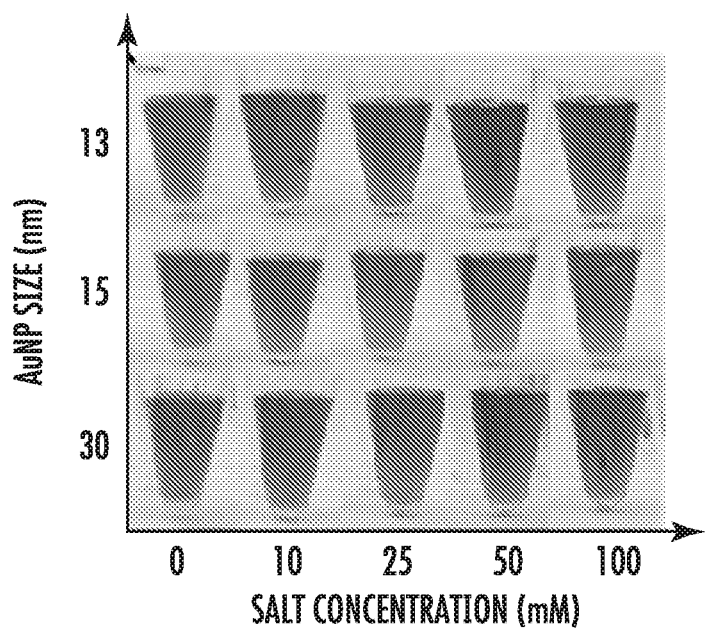
FIG. 7 shows a color change experiment for different sized AuNPs. (A) Digital image of change in color with size and salt concentration. (B) Digital image of change in color for 13 nm AuNPs. (C) DLS analysis of aggregated particles. (D) The UV-visible absorbance intensity for 13 nm AuNPs at 520 nm.

In the Examples above, gold nanoparticles (AuNPs) of two different sizes (15 nm and 30 nm) were thoroughly characterized in terms of hydrodynamic and crystallite size, surface charge and surface presence of any molecule/s. In this Example, another set of AuNPs of size 13 nm were synthesized and thoroughly characterized. The characterization of the 13 nm particles is shown in FIG. 6. The aggregation of all three AuNPs was studied in presence of different concentration of salt (NaCl; 0, 10, 25, 50 and 100 mM). The concentration for all three AuNPs was kept similar for this experiment. FIG. 7A shows the color change with increasing the salt concentrations. The color change was observed at 25 mM for all the three nanoparticles, further increase resulted in blue to purple color. Thirteen (13) nm AuNPs have a more intense color change compared to the others. This high intensity is explained by the lower surface charge (13 nm→−21.9 mV; 15 nm→−28.23 mV; and 30 nm→−30.13 mV) and smaller size (higher surface energy) of the 13 nm AuNPs, which induces higher agglomeration in presence of salt as compared to other AuNPs.

Figure 7B:
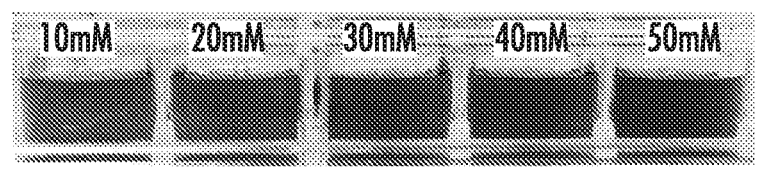
Figure 7C:
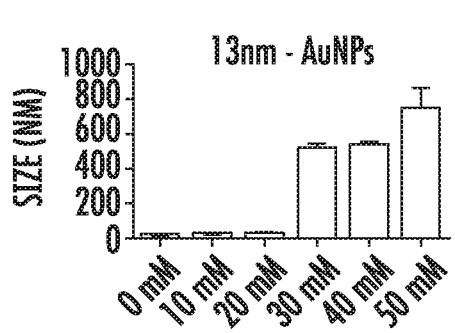
Figure 7D:
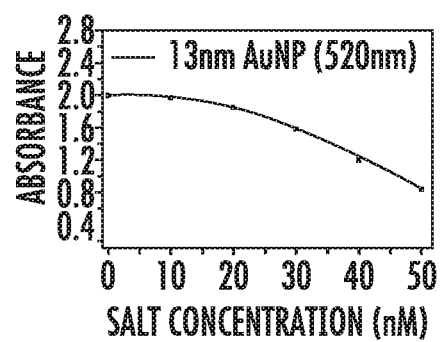

As the color change was seen at 25 mM (no change at 10 mM), another experiment was out carried to determine the exact NaCl concentrations (smaller range) needed for inducing agglomeration (10-50 mM). FIGS. 7B, C and D show the color change (B), hydrodynamic size (C) and absorbance at 520 nm (D) with addition of salts, respectively. The color change due to aggregation of the nanoparticles was prominent, when salt was 30 mM or more. The results were supported by dynamic light scattering data (DLS) analysis. It can be seen that there is sudden increase in size at 30 mM salt concentration. It was also observed that there is a decrease in optical density at 520 nm due to the red-shift in UV-vis spectra in all the different concentrations of the AuNPs. It was observed that the size of the aggregates for 13 nm particles increased up to 800 nm.

Example 10. Analysis of Mosquito Feeding Solution

Figure 8:
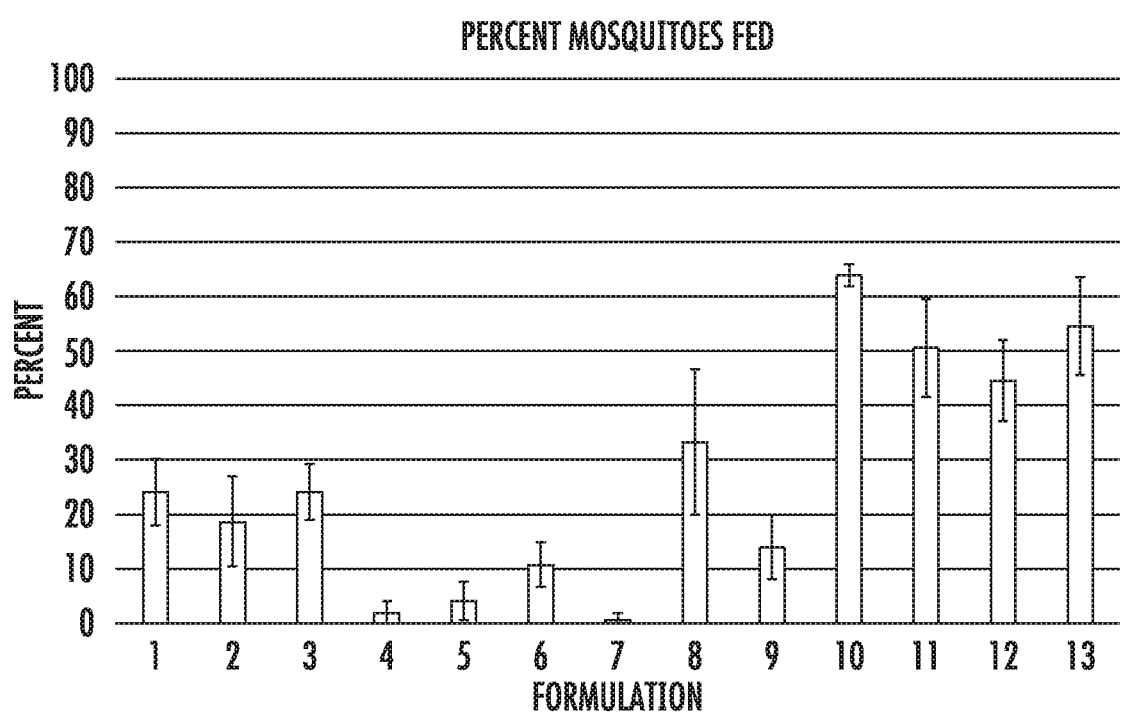
FIG. 8 is a chart of the average percent of female *Ae. aegypti* that fed when provided various feeding solution formulations for 2 hours. The formulations as described in Table 2 of Example 10 below.

Experiments were performed to analyze the feeding solution composition for the aptamer working solution. Small cups of mosquitoes (50 female *Ae. aegypti* mosquitoes/cup) were supplied with a different feeding solution formulation listed in Table 2 for 2 h. Three repeats were conducted for each formulation for a total of 150 mosquitoes. The results of this experiment are detailed in Table 2 and FIG. 8.

TABLE 2

Mosquito feeding solution formulations tested

| Formulation | Sucrose | NaCl | NaHCO₃ | MgCl₂ | ATP-Na | ATP-b-y, met | AuNP |
|---|---|---|---|---|---|---|---|
| 1 | 10% | x | x | 1 uM | x | x | 50% |
| 2 | 10% | x | x | 1 uM | 100 uM | x | 50% |
| 3 | 10% | x | x | 1 uM | x | 5 uM | 50% |
| 4 | x | x | x | 1 uM | 100 uM | x | 50% |
| 5 | x | x | x | 1 uM | x | 5 uM | 50% |
| 6 | x | 150 mM | 10 mM | 1 uM | 100 uM | x | 50% |
| 7 | x | 150 mM | 10 mM | 1 uM | x | 5 uM | 50% |
| 8 | x | 15 mM | 1 mM | 1 uM | 100 uM | x | 50% |
| 9 | x | 15 mM | 1 mM | 1 uM | x | 5 uM | 50% |
| 10 | 10% | 15 mM | 1 mM | 1 uM | 100 uM | x | 50% |
| 11 | 10% | 15 mM | 1 mM | 1 uM | x | 5 uM | 50% |
| 12 | 10% | x | x | 1 mM | 100 uM | x | 50% |
| 13 | 10% | x | x | 1 mM | x | 5 uM | 50% |

Example 11. Analysis of Gold-Aptamer Nanoparticles

The Au-aptamer conjugates were analyzed with the gold nanoparticles and test aptamers to detect epinephrine with high sensitivity. The aptamer concentration was varied from 0.02 nm to 2 µm to determine the optimum concentration. As a negative control, ascorbic acid was used due to its close structural similarity and electrochemical properties.

Gold Nanoparticles (13 nm) were synthesized using the standard procedure of citrate reduction of $HAuCl_4$. The 32-mer 5'-aptamer-Thiol-3' and unmodified aptamer specific to epinephrine were designed and synthesized by BasePair-Bio Company. Epinephrine was purchased from Sigma-Aldrich. The experiment was performed with 1 mM PBS consisting of 0.1 mM $MgCl_2$.

Cryopreserved aptamers were brought to room temperature and diluted to the required concentrations (0.02 nM-2 µM) using the buffer solution. The aptamers were then refolded by incubating at 95° C. for 15 min and kept at room temperature for another 15 min. AuNPs-aptamer complexes were prepared by mixing the gold nanoparticle solution and folded aptamer in 1:1 ratio. Different concentrations of epinephrine (90 µM (500 ng), 63 µM (350 ng), 36 µM (200 ng), 9 µM (50 ng), 0.9 µM (5 ng), 9 µM (0.5 ng)) were tested. Next, salt (300 µM NaCl) was added to the sample to amplify the agglomeration and result in further visual color change.

UV-Visible spectroscopy of 13 nm AuNPs conjugated with different concentrations of the aptamer was performed. The response to the different aptamer concentrations for the individual concentration of the epinephrine was analyzed. The surface Plasmon peak of AuNPs at 520 nm broadens and shifts to a longer wavelength as a function of the concentration of epinephrine. Peak broadening and the presence of a peak at ~620 nm is indicative of Au-aptamer aggregation. It was observed that increasing the concentration of epinephrine increased the aggregation in the solution and resulted in a blue solution color. The results demonstrate that the increase in aptamer concentration affects the detection limit of epinephrine. This effect is due to excess free aptamer in the solution binding to epinephrine, inhibiting the aggregation of the AuNPs and thus affecting the sensitivity of the sensor. In one embodiment, the range of aptamer for maximum detection of the analyte is between 2 nM and 20 nM, which can detect epinephrine levels as low as 50 ng. Specificity experiments with 2 nM of Au-aptamer conjugates and the negative control L-ascorbic acid illustrate that the non-target control produces no observable color change while increasing levels of epinephrine yielded increase shift in solution color from red to blue.

We claim:

1. A device comprising:
   (a) an internal payload reservoir comprising a payload solution, wherein the payload solution comprises:
      (i) an insect attractant or insect food source, wherein the insect attractant or insect food source is sugar water; and
      (ii) a detector conjugate comprising a gold nanoparticle conjugated to a specific detector molecule that binds specifically to a protein present in the saliva of a specific insect to be detected, wherein the specific detector molecule is an aptamer;
   (b) an internal transfer wick;
   (c) a secondary reservoir; and
   (d) an outer releasing wick;
   where the internal payload reservoir comprising the payload solution is contained within the secondary reservoir that is within the outer releasing wick; and wherein the internal transfer wick transfers the payload solution via the secondary reservoir to the outer releasing wick that envelops the device and enables release of the payload solution.

2. The device of claim 1, further comprising a toxic sugar water sub stance.

3. The device of claim 1, wherein the specific insect is selected from the group consisting of mosquitoes, flies, sand flies, tsetse flies, black flies, ticks, lice, midges, fleas, ticks, mites, and triatomine bugs.

4. The device of claim 3, wherein the specific insect is a mosquito.

5. The device of claim 4, wherein the mosquito is selected from the group consisting of Aedes (Ae.) aegypti, Ae. vexans, Ae. albopictus, Ae. togoi, Ae. triseriatus, Ae. arabiensis, Culex (Cx.) quinquefasciatus, Cx. pipiens, Cx. tarsalis, Anopheles (An.) sinensis, Anopheles gambiae, and Culiseta (Cs.) inornata.

6. A device comprising:
   (a) an internal payload reservoir comprising a payload solution, wherein the payload solution comprises:
      (i) an insect attractant or insect food source, wherein the insect attractant or insect food source is sugar water;
      (ii) a detector conjugate comprising a gold nanoparticle conjugated to a specific detector molecule that binds specifically to a pathogen protein present in the saliva of an insect infected by a pathogen, wherein the specific detector molecule is an aptamer;
   (b) an internal transfer wick;
   (c) a secondary reservoir; and
   (d) an outer releasing wick;
   where the internal payload reservoir comprising the payload solution is contained within the secondary reservoir that is within the outer releasing wick; and wherein the internal transfer wick transfers the payload solution via the secondary reservoir to the outer releasing wick that envelops the device and enables release of the payload solution.

7. The device of claim 6, further comprising a toxic sugar water substance.

8. The device of claim 6, wherein the specific insect is selected from the group consisting of mosquitoes, flies, sand flies, tsetse flies, black flies, ticks, lice, midges, fleas, ticks, mites, and triatomine bugs.

9. The device of claim 8, wherein the specific insect is a mosquito.

10. The device of claim 9, wherein the mosquito is selected from the group consisting of Aedes (Ae.) aegypti, Ae. vexans, Ae. albopictus, Ae. togoi, Ae. triseriatus, Ae. arabiensis, Culex (Cx.) quinquefasciatus, Cx. pipiens, Cx. tarsalis, Anopheles (An.) sinensis, Anopheles gambiae, and Culiseta (Cs.) inornata.

11. The device of claim 6, wherein the pathogen protein is from an arbovirus.

12. The device of claim 11, wherein the pathogen protein is from dengue virus, chikungunya virus, or Zika virus.

* * * * *